(12) United States Patent
Biser

(10) Patent No.: US 8,784,391 B1
(45) Date of Patent: Jul. 22, 2014

(54) THERAPEUTIC COMPRESS SYSTEM AND METHODS OF USE

(76) Inventor: Seth Biser, Fleetwood, NY (US)

(*) Notice: Subject to any disclaimer, the term of this patent is extended or adjusted under 35 U.S.C. 154(b) by 101 days.

(21) Appl. No.: 13/298,445

(22) Filed: Nov. 17, 2011

Related U.S. Application Data

(60) Provisional application No. 61/415,153, filed on Nov. 18, 2010.

(51) Int. Cl.
*A61M 35/00* (2006.01)
*A61F 7/00* (2006.01)

(52) U.S. Cl.
USPC ............................ 604/294; 607/109; 607/112

(58) Field of Classification Search
USPC .......... 604/293–304; 601/37; 351/142; 2/6.3, 2/15, 173, 426–454; 607/108–112, 114
See application file for complete search history.

(56) References Cited

U.S. PATENT DOCUMENTS

| | | | |
|---|---|---|---|
| 2,237,971 A * | 4/1941 | Padelford ...................... | 607/109 |
| 2,586,851 A * | 2/1952 | Monro et al. ............ | 128/201.19 |
| 4,190,054 A | 2/1980 | Brennan | |
| 4,243,041 A | 1/1981 | Paul | |
| 5,545,197 A | 8/1996 | Bowen | |
| 6,138,286 A * | 10/2000 | Robrahn et al. .................. | 2/436 |
| 6,241,711 B1 | 6/2001 | Weissberg et al. | |
| 6,316,687 B1 | 11/2001 | Davis et al. | |
| 6,589,272 B1 | 7/2003 | Sheikh | |
| 2001/0039442 A1 | 11/2001 | Gorge et al. | |
| 2005/0187502 A1 | 8/2005 | Krempel et al. | |
| 2009/0287282 A1 | 11/2009 | Biser et al. | |
| 2009/0287283 A1 | 11/2009 | Biser et al. | |
| 2011/0178585 A1 | 7/2011 | Biser et al. | |

FOREIGN PATENT DOCUMENTS

| | | |
|---|---|---|
| JP | S63-62119 A1 | 4/1988 |
| JP | 10211228 A1 | 8/1998 |
| JP | 2000116430 A1 | 4/2000 |
| JP | 2004350803 A1 | 12/2004 |
| WO | 01/39704 A1 | 6/2001 |
| WO | 2009140673 A1 | 11/2009 |

OTHER PUBLICATIONS

Written Opinion of related PCT application US2009/044327, Jul. 16, 2009. File name 20120315_13-298445_NPL_Cite1.pdf.

(Continued)

*Primary Examiner* — Melanie Hand
*Assistant Examiner* — Ned T Heffner
(74) *Attorney, Agent, or Firm* — John M. Hammond; Patent Innovations LLC

(57) ABSTRACT

A therapeutic compress system for treatment of a body part. For treatment of the eye region, the compress system comprises a deformable frame that is disposable upon the eye region and includes a first frame section joined to a second frame section at a central bridge. A gel pack is removably joined to the frame and comprises a gelatinous material contained in a pouch. A V-strap assembly may be required for securing the gel pack and frame to the eye user in a manner that optimizes pressure of the gel pack on the eye region and comfort of the user. The compress system may include a gel impressor that is inwardly deformable so as to contact portions of the gel pack with the nasal corners of the eyes of the user.

25 Claims, 11 Drawing Sheets

(56) References Cited

OTHER PUBLICATIONS

Spa Necessities "Moist Heat Therapy" Eye Warming Pillow sold at http://www.amazon.com/Moist-Heat-Therapy-Warming-Pillow/dp/B0000ZH3F0?SubscriptionId=1GKMRWT8RXFTWF55P882&tag=lightingelect-20&linkCode=xm2&camp=2025&creative=165953&creativeASIN=B0000ZH3F0. File name 20120315_13-298445_NPL_Cite2.pdf. Date on website Feb. 2, 2009; earliest posting date unknown.

Brookstone Eye Mask shown and reviewed at http://www.buzzillions.com/reviews/brookstone-hot-cold-anti-stress-sinus-mask-reviews. File name 20120315_13-298445_NPL_Cite3.pdf. Date on website Jan. 9, 2009; earliest posting date unknown.

Thermalon Dry Eye Compress sold at http://www.amazon.com/Thermalon-24342-Dry-Eye-Compress/dp/B004385RPS/ref=sr_1_1?s=hpc&ie=UTF8&gid=1321925614&sr=1-1. File name 20120315_13-298445_NPL_Cite4. Date on website Sep. 30, 2011; earliest posting date unknown.

Elasto-Gel eye mask sold at http://www.amazon.com/Elasto-Hot-Cold-Sinus-Mask/dp/B000FHZNQE/ref=pd_sim_hpc_5. File name 20120315_13-298445_NPL_Cite5. Date on website Oct. 5, 2007; earliest posting date unknown.

Corso EyesPack sold at http://www.eyespack.com/eyespack.html. File name 20120315_13-298445_NPL_Cite6. Copyright date on website 2009; earliest posting date unknown.

The Body Shop Eye Gel Pack sold at http://www.totalbeauty.com/reviews/product/6096441/the-body-shop-eye-gel-mask. File name 20120315_13-298445_NPL_Cite7. Date on website ~May 2008; earliest posting date unknown.

R&R Soft ColdHot Soothing Mask sold at http://www.taiwanstanch.com/product_explanationE.asp?kind=90&id=185&Page=1. File name 20120315_13-298445_NPL_Cite8. Earliest posting date unknown.

Gel Eye Mask (generic) sold at http://hzvison.en.made-in-china.com/product/weEQGmfcgkhH/China-Gel-Eye-Mask-VS-TRM01-.html. File name 20120315_13-298445_NPL_Cite9. Earliest posting date unknown.

Gel Pack sold at http://www.accurategelpacks.com/eye_mask.html. File name 20120315_13-298445_NPL_Cite10. Earliest posting date unknown.

OCuSOFT Lid Scrub Pads for eyelid cleansing sold at http://www.ocusoft.com/730-1-90.html. File name 20120315_13-298445_NPL_Cite11. Copyright date on website 2009; earliest posting date unknown.

Office Action of Jun. 9, 2011 in related U.S. Appl. No. 12/153,321. File name 20120315_13-298445_NPL_Cite12.

* cited by examiner

THERAPEUTIC COMPRESS SYSTEM AND METHODS OF USE

CROSS-REFERENCE TO RELATED PATENT APPLICATIONS

This application claims priority from U.S. Provisional Patent Application No. 61/415,153 filed Nov. 18, 2010, the disclosure of which is incorporated herein by reference.

This application is also related to commonly owned copending U.S. patent application Ser. No. 12/153,321, filed on May 16, 2008; commonly owned U.S. patent application Ser. No. 12/153,322, also filed on May 16, 2008; and commonly owned PCT Application No. PCT/US2009/044327, filed on May 18, 2009, the disclosures of which are incorporated herein by reference.

BACKGROUND

1. Field of the Invention

The inventions disclosed herein are directed to compress devices, kits, assemblies, system, and methods of using such to provide therapeutic benefit to a portion of a user's body. More particularly, the inventions may be used to provide therapeutic benefit to the eye region of a user by the application or removal of thermal energy, and/or by the application of a therapeutic agent.

2. Description of Related Art

Both hot and cold compresses play an important role in treating various physical problems. In the most common and traditional "do-it-yourself" method of compress therapy, a user holds a washcloth either under hot or cold running tap water, or in a basin of hot or cold water, and then applies the moist, temperature-adjusted washcloth to the body part.

Other efforts to apply sustained thermal application as a part of compress therapy are also known. One example is a gel pack, which can be heated or cooled, and applied against a user's body. Known gel packs designed specifically for use on the eyes and periorbital regions have been manufactured with casings made of polyvinyl chloride materials (also known as PVC or vinyl), which have the benefit of low production costs. However, such casing materials have various characteristics that limit their effectiveness for ocular thermal therapy.

Additionally, to the best of the Applicants' knowledge, known gel packs either alone or in combination with related fixturing, also fail to provide an optimally adjustable, comfortable, and desired degree of compression of the gel pack against the eye, the eye region, or another body part being treated. Such known gel packs do not enable a user to select the manner in which the external pressure is applied against the body part, nor the amount of external pressure that is applied to the body part, nor do they address the specific anatomic challenges of fitting devices to the body region in question.

Accordingly, there remains a need for a thermally and mechanically adjustable compress system which will impart comfortable and effective therapy to sensitive body parts, such as the eye region, in a safe and convenient manner.

SUMMARY

The present invention meets this need by providing therapeutic compress systems and methods for their use. In certain embodiments, the compress systems may be configured to provide therapy to the eye region of a user. The compress systems may be thermal compress systems and provide heating or cooling to the eye region. Alternatively or additionally, the compress systems may provide a therapeutic agent to the eye region or to one or both of the eyes of a user.

A compress system according to the present disclosure includes a deformable frame and a gel pack. The compress system may further include a strap assembly for securing the frame and gel pack to a body part of the user, such as the eye region.

The deformable frame supports the gel pack. The frame may be made of a plastic that is sufficiently thick enough such that it will not buckle when supporting the weight of the gel pack in an upright position when used by the user in a sitting-up position, while also being sufficiently deformable so as to conform to the eye region of the user when fitted thereto.

The frame may be attached to a head strap assembly. The frame may have attachments for members of the strap assembly along its side edges, and attachments for the gel pack along its top edge. In that manner, the strap members provide rearward compression of the frame toward the eyes, but the strap members do not directly pull the gel pack back against the eyes. This prevents certain creases from forming in the gel pack in ways that impart uncomfortable pressure against the eyes.

The frame may be provided with open eye apertures. This allows the user to adjust the gel pack directly by finger contact through the apertures. The apertures also have an unexpected advantage of relieving or limiting the pressure of the gel pack against the eyes, when compared to an identical frame that is not fitted with such apertures. The strap assembly may be provided in a V-shaped configuration, which splits up the vector forces of the strap above and below the eyes, thereby reducing pressure directly upon the eyes. The members of the head strap assembly are attached at pivoting points, both to each other and to the frame.

The gel pack may be provided as removable from the external frame. Male and female snaps may be used to attach the gel pack to the external frame. The gel pack is preferably made of a nylon material, rather than a PVC-like material. Although the nylon material may be more difficult to fabricate into a gel pack, the Applicants have discovered that nylon materials have several advantages over PVC-like materials in achieving gentle thermal pressure against a body part. Nylon materials are stronger and provide greater protection against holes or defects in the gel pack; they allow more transmission of heat from the gel to the body part, both because thinner materials can be used (due to their increased strength) and because they may provide better heat conductivity; and nylon material can be safely heated in a microwave oven, whereas users are often warned against putting vinyl and PVC-like materials into microwave ovens.

A "gel impressor" device, made of a deformable strip, may be attached at the center bridge of the frame, allowing the user to deform the strip inwardly and thereby press the gel inwardly so it exerts more pressure directly in the nasal corners of the eyes (also known as the nasal canthal region).

More specifically, according to the present disclosure, a compress system is provided comprising a deformable frame disposable upon the eye region of a human and comprising an inner or rear side and an outer or front side, and a first frame section joined to a second frame section at a central bridge. A gel pack is removably joined to the frame and comprises a gelatinous material contained in a pouch. The pouch may be comprised of a first sheet of material joined to a second sheet of material at a seal formed at the perimeters of the first and second sheets of material. A first fastener removably joins the gel pack to a first mating fastener on the inner side of one of the first and second frame sections, at a first inward indentation in the seal. The first fastener and first mating fastener may be a first upper fastener removably joining the gel pack to a first mating upper fastener on the inner side of the first frame section, at the first inward indentation in the seal.

In like manner, a second upper fastener removably joins the gel pack to a first mating upper fastener on the inner side of the second frame section, at a second inward indentation in the seal. A first lower fastener removably joins the gel pack to a first mating lower fastener on the inner side of the first frame section, at a third inward indentation in the seal. In like manner, a second lower fastener removably joins the gel pack to a first mating lower fastener on the inner side of the second frame section, at a fourth inward indentation in the seal.

Each of the fastener and mating fasteners may be snap assemblies. The first mating upper fastener on the inner side of the first frame section may be a first snap piece disposed in a recessed cavity formed in on the inner side of the first frame section, and the first mating upper fastener on the inner side of the second frame section may be a second snap piece disposed in a recessed cavity formed in on the inner side of the second frame section. By placing the snap pieces in recessed cavities, the corresponding snap pieces that are connected to them to join the gel pack to the frame do not protrude as much, thereby providing greater comfort to the user.

The first and second upper fasteners and the first and second lower fasteners may be snap pieces to mate with corresponding snap pieces on the frame. Each of the snap pieces may have a diameter greater than the distance across the respective inward indentations in the seal of the gel pack. In that manner, less stress to the gel pack wall occurs when a user grabs the gel pack and forcibly pulls it from the frame, thereby avoiding damage to the gel pack, and possible leakage of the gel contained therein.

The distance between the third inward indentation in the seal and the fourth inward indentation in the seal when the gel pack is not joined to the frame may be greater than the distance between the first mating lower fastener on the inner side of the first frame section and the first mating lower fastener on the inner side of the second frame section. In that manner, when the gel pack is joined to the frame by the fasteners which are located at the indentations in the seal, a relaxed fit of the gel pack is provided, such that it is not taut across the eyes of the user, thereby providing greater comfort to the user and better conformance of the gel pack to the eyes.

Also according to the present disclosure, a support assembly for a compress system is provided comprising a deformable frame disposable upon the eye region of a human and comprising an inner side and an outer side, and a first frame section joined to a second frame section at a central bridge; and a strap assembly. On a first side of the frame, the strap assembly is comprised of a first V-subassembly comprising a first inelastic upper member pivotably joined at an inner end thereof to an upper lateral portion of the first frame section, and including an outer end, and a first elastic lower member pivotably joined at an inner end thereof to a lower lateral portion of the first frame section and joined at an outer end thereof to the outer end of the first inelastic member. In like manner, on a second side of the frame, the strap assembly is comprised of a second V-subassembly comprised of a second inelastic upper member pivotably joined at an inner end thereof to an upper lateral portion of the second frame section, and including an outer end, and a second elastic lower member pivotably joined at an inner end thereof to a lower lateral portion of the second frame section and joined at an outer end thereof to the outer end of the second inelastic member. A connecting strap joins to the outer end of the first inelastic member and the outer end of the second inelastic member, thereby providing a complete strap assembly to secure the compress system to the head and eye region of the user.

Also according to the present disclosure, a compress system is provided comprising a deformable frame disposable upon the eye region of a human and comprising an inner side and an outer side, and a first frame section joined to a second frame section at a central bridge; and an impressor joined to and extending laterally across the central bridge of the frame. The impressor is comprised of a deformable plate of material including a first portion extending over an aperture in the first frame section, and second portion extending over an aperture in the second frame section. The first and second portions are inwardly deformable so as to contact respective first and second portions of a gel pack that may be removably joined to the deformable frame. By deforming the impressor, the first and second portions of the gel pack are displaced toward the nasal corners of the eyes of a user.

BRIEF DESCRIPTION OF THE DRAWINGS

The present disclosure will be provided with reference to the following drawings, in which like numerals refer to like elements, and in which.

Figure 1:
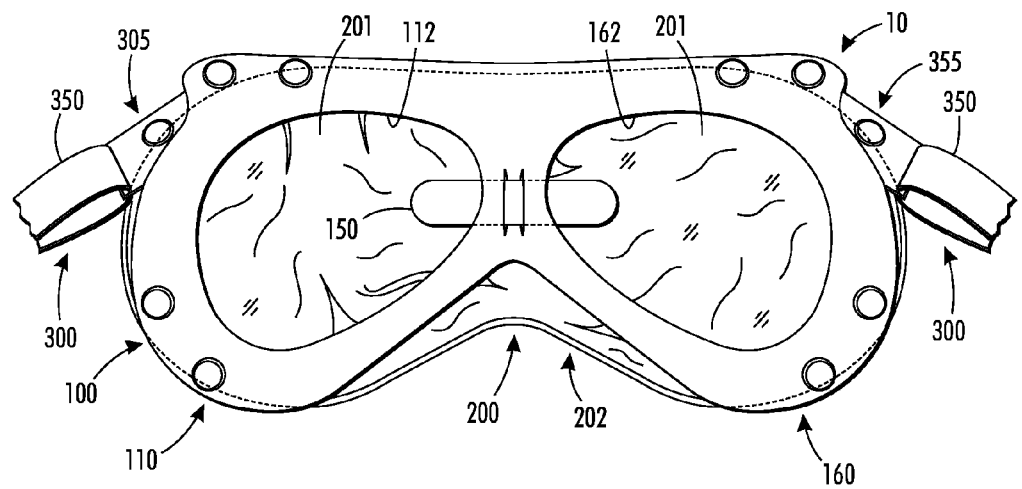
FIG. 1 is a front view of a thermal compress system for the eye region of a user, the system comprising a frame, a gel pack, a strap assembly.

The present invention will be described in connection with certain preferred embodiments. However, it is to be understood that there is no intent to limit the invention to the embodiments described. On the contrary, the intent is to cover all alternatives, modifications, and equivalents as may be included within the spirit and scope of the invention as defined by the claims.

DETAILED DESCRIPTION

For a general understanding of the present invention, reference is made to the drawings. In the drawings, like reference numerals have been used throughout to designate identical elements.

The inventions disclosed herein are directed to, for example, thermally adjustable body compress devices, assemblies, kits, systems, and methods of preparing and using the same. The devices and methods can be used to treat or alleviate a variety of abnormal physiological conditions in users, or to provide therapeutic benefit to users who are otherwise in normal condition. The devices and methods can be applied to various body parts such as, for example, the soft tissues, muscles, bones, and other tissues and organs of a user. Although embodiments will be described with relation to applying the compress devices and methods to an eye region of a user, it is understood that other embodiments have broader application to other parts of the anatomy. Accordingly, the inventions disclosed herein are not to be construed as being limited only to use in treatments of the eye or eye region of a user. The inventions are adaptable to any use in which thermal or other surface treatment is desirable to be provided by contacting a body part of a user with a compress that may transfer thermal energy to or receive thermal energy from the body part, and/or that may transfer a therapeutic agent to the body part.

As used herein, the term "user" includes mammalian subjects including humans. Additionally, the description identifies certain components with the adjectives "top," "upper," "bottom," "lower," "left," "right," "front," "rear," etc. These adjectives are provided in the context of use of a compress system in therapy of the eye region of a user, and in the context of the orientation of the drawings that show an upright human user. In this context, the terms "top," "bottom," "left," "right," "front," and "back" refer to the orientation of the gel pack and compress assembly in relation to the user, in an applied position on the user's face when the user is standing upright (a position known in the art as the "anatomical position") and facing out of the page toward the viewer. The compress systems disclosed herein can be used either in an upright (sitting or standing) or recumbent position. The front side of the system is the side that faces outwardly and is the side illustrated in FIG. 1. The back side is the opposite side of the gel pack which faces the user in an applied position of the gel pack (i.e. when the gel pack is in use) and is the side illustrated in FIG. 2.

In some embodiments, an eye region of a user that is treated by devices and methods described herein includes the periocular region. The periocular region is defined as including the eyelid, including the skin of the upper and lower eyelids; the eyelid margins; and the lateral canthus and the medial canthus. In other embodiments, the eye region includes the periorbital region. The periorbital region is defined as including the lower brow region, the upper cheek region, the bridge of the nose, and at least a portion of the temple of the head. In other embodiments, the eye region includes both the periocular region and the periorbital region. The above described anatomical sites are described in the singular tense but it is understood that these regions are bilateral and thus embodiments can also cover both the left and right periocular and/or periorbital regions. In some embodiments, the eye region includes the entire temple(s) of the head.

Figure 2:
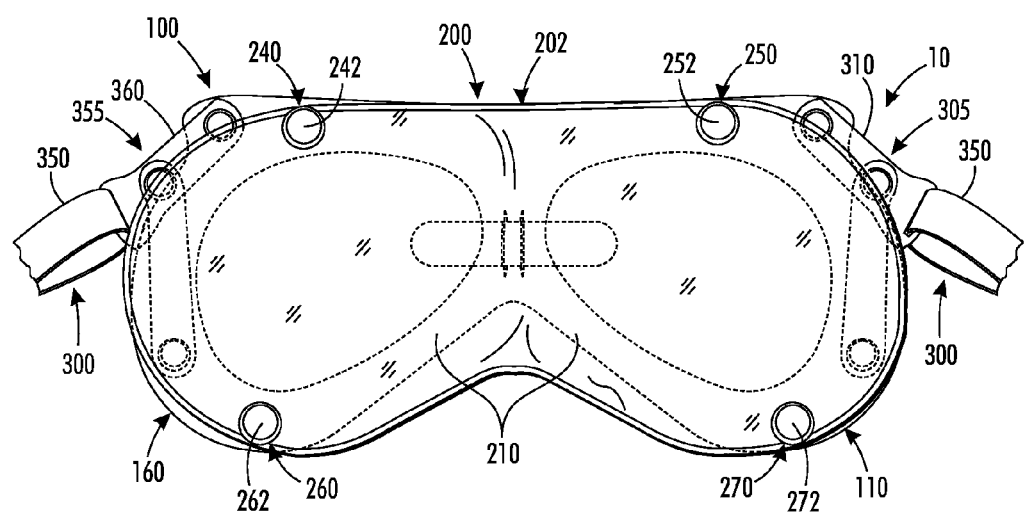
FIG. 2 is a rear view of the thermal compress system of FIG. 1.

FIGS. 1 and 2 show a compress system 10 having a pack 200 configured to be applied against the eye region of a user's face. The pack 200 may be provided as a thermally adjustable pack that has been pre-heated or pre-chilled sufficiently so as to apply heat to or remove heat from the user's eye region in order to provide a therapeutic benefit to the user. Accordingly, pack 200 comprises a substance with a substantial heat capacity, the temperature of which can be regulated or adjusted by applying various degrees of heat or cold. Such a substance is capable, at a minimum, of being warmed or cooled so that it achieves a temperature that is substantially different from the ambient temperature of the environment, and sustains the achieved temperature for a relatively long period of time and with a relatively slow period of decline back toward ambient temperature. In some embodiments, for example, 2.5 ounces of such a substance can be heated to 135° F. and will still have a temperature of at least 115° F. after 5 minutes of exposure to 72° F. air. Alternatively, the substance may store and/or release its thermal energy in whole or in part by a phase change in which latent heat is released or absorbed. Alternatively, the substance may release thermal energy by the initiation of an exothermic reaction.

Non-limiting examples of thermally activatable substances include water and other fluids; various gelatinous materials such as solid or semi-solid gels, including solutions containing sodium acetate trihydrate, which can be chemically activated with a nucleation center or other means to produce an exothermic reaction; dried vegetables and cereals such as rice, beans, corn, and peas; water-containing food products such as potatoes and apples; and various other vegetables and food products. In some embodiments, the thermally activatable substance is a gelatinous substance 201 (also referred to herein as a "gel" or "gelatinous material") and the thermally activatable pack is a gel pack 202. The embodiments disclosed subsequently herein will be described with respect to a gelatinous substance, although it is to be understood that other thermally activatable substances can also be used.

Referring again to FIGS. 1 and 2, a compress system 10 is shown, which is comprised of a frame 100, a gel pack 202, and a strap assembly 300 comprising a first V-subassembly 310, a second V-subassembly 360, and a connecting strap 350.

Figure 3:
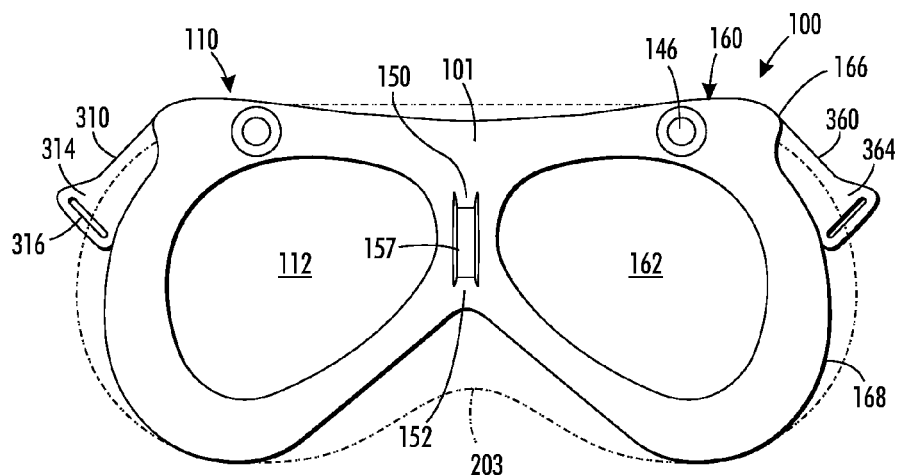
FIG. 3 is a front view of the frame for holding a gel pack against the eye region of a user.
Figure 4:
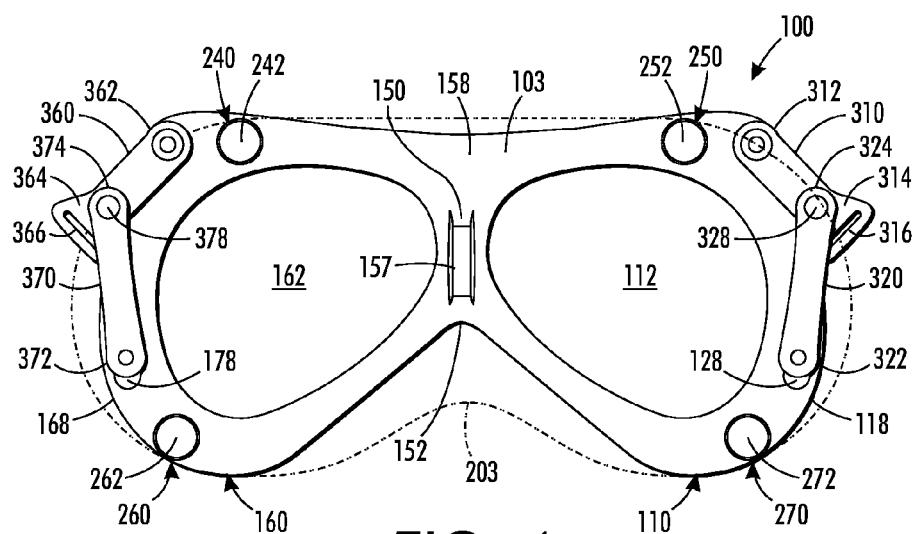
FIG. 4 is a rear view of the frame of FIG. 3.

FIG. 3 is a front view of the frame 100 for holding the gel pack 202 against the eye region of a user, and FIG. 4 is a rear view of the frame 100. In FIGS. 3 and 4, the perimeter edge 203 of a gel pack 202 is also shown in dotted line format to depict the positions of the frame 100 and gel pack 202 relative to each other. Referring to FIGS. 1-4, the frame 100 is made of a material that is sufficiently thick enough such that it will not buckle when supporting the weight of the gel pack 202 in an upright position when used by the user in a sitting-up position (see FIGS. 7 and 8), while also being sufficiently deformable or bendable so as to conform to the eye region of the user when fitted thereto. The deformable frame material may be a plastic, such as e.g., polypropylene, polyethylene, high density polyethylene (HDPE), or low density polyethylene (LDPE). The choice of plastic material is dependent upon the thickness of the plastic, the combination of which is selected so as to provide sufficient flexibility to conform to the eye region of a user, while not substantially buckling, folding over on itself, or creasing in an uncontrolled manner when supporting the weight of the gel pack 202 when used by a user in a sitting-up position.

In one embodiment, the frame 100 may be made of polypropylene plastic having a thickness of about 0.030 inches. In another embodiment, the frame 100 may be made of HDPE plastic having a thickness of about 0.035 inches. In another embodiment, the frame 100 may be made of LDPE plastic having a thickness of between about 0.035 inches and about 0.060 inches. In particular, the frame may have an LDPE thickness of about 0.050 inches.

In one embodiment in which the gel pack being supported had a maximum weight of less than 4 ounces and had a maximum width of approximately 8.5 inches, a frame material of 0.030" polypropylene (PP) was stiff enough to support the full gravitational weight of the gel pack when the frame was held perpendicularly by its bottom edge and not applied to a body part. In another embodiment in which gel pack 202 had a maximum weight of around 7.2 ounces and a maximum width of approximately 10 inches, a frame 100 made of 0.050" low-density polyethylene (LDPE) was not stiff enough to fully support the full gravitational weight of the gel pack when the frame was supported perpendicularly by its bottom edge, but not applied to a body part. This frame 100 made of 0.050" LDPE began to buckle slightly under these circumstances. However, this frame 100 did not substantially buckle, fold over on itself, or crease in an uncontrolled manner when used in an applied position against a user's face, and therefore was suitable for use by the user. Thus, the Applicants have discovered that the frame material can include a wider variety of deformable materials than previously thought based on prior experience. By example not intended to be limiting, a variety of fabrics, foams, paper materials, soft plastics, and other materials may be used as frame materials, provided that they do not buckle when supporting the weight of the gel pack 202 in an upright position when used by the user in a sitting-up position, and are sufficiently deformable or bendable so as to conform to the eye region of the user when fitted thereto.

In its free state (i.e., not deformed against the eye region of a user) the frame 100 may be a substantially flat structure having an outer or front side 101 and an inner or rear side 103. In one embodiment, the frame 100 in its free state may be a planar structure. In another embodiment (not shown), the frame 100 in its free state may be substantially planar except in the lower bridge region 152 and the upper bridge region 158. This region 152 may be deformed forwardly out of the plane so as to provide a relief for the user's upper nasal area, thereby providing better comfort and conformance to the user's face. The upper bridge region 158 may also be deformed forwardly out of the plane so as to lessen any excess pressure that would be placed on the forehead region when the lower bridge region 152 is deformed outwardly.

The frame 100 is comprised of a first frame section 110 joined to a second frame section 160 at a central bridge 150. The first and second frame sections 110 and 160 may be provided with respective oblong apertures 112 and 162. In that manner, a user may adjust the fit of the gel pack to the eyes by contacting the gel pack directly with the fingers. Additionally, the user may adjust the bend of a gel impressor 151 against the gel pack 202, as will be explained subsequently herein.

The apertures 112 and 162 also have the unexpected benefit of producing a greater degree of comfort to users when used with gel pack 202, relative to an identical frame 100 that was made without such apertures 112 and 162. Without wishing to be bound by theory, it is likely that the apertures 112 and 162 prevent the gel pack 202 from applying too much pressure to the eyes, relative to an identical frame 100 that could be made without such apertures 112 and 162. However, it is also possible that the apertures allow a greater buildup of gel material directly over the apertures (because this area is not flattened-down by the material in the frame). The approach of using apertures in a body compress system is in contrast with typical compress system art for application to various body parts, which systems do not provide apertures for pressure relief. In most compress systems, firm pressure of the gel pack against the entire body part underlying the compressive element is desired.

Figure 5A:
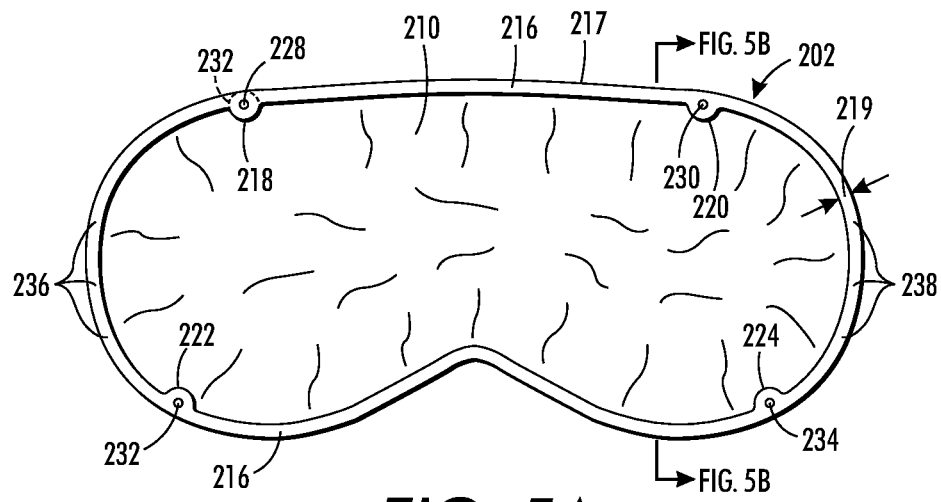
FIG. 5A is a rear view of a gel pack including a perimeter seal, the gel pack being removably attachable to the frame of FIGS. 3 and 4.
Figure 5B:
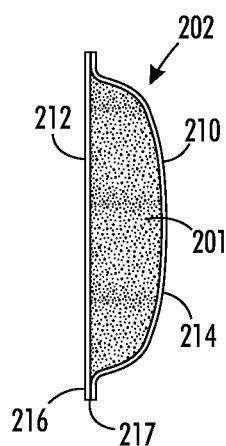
FIG. 5B is a cross sectional view of a thin slice of the gel pack of FIG. 5A, taken between the closely spaced parallel lines 5B-5B.
Figure 6A:
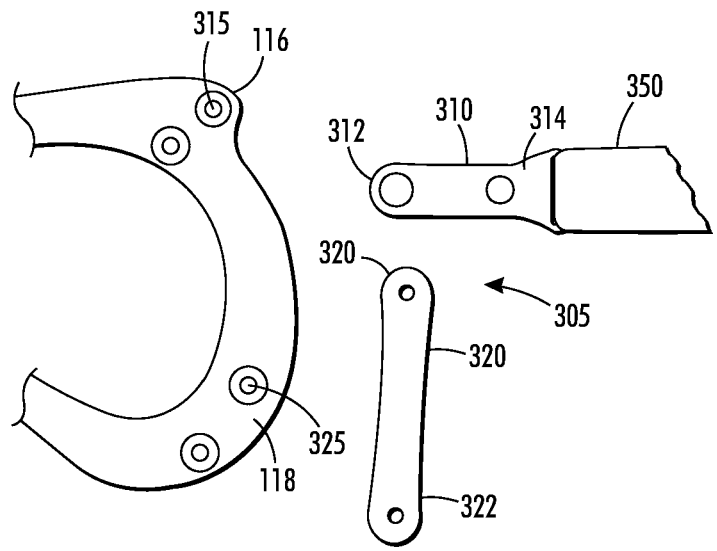
FIG. 6A is an exploded view of a portion of the frame of FIGS. 3 and 4, and a portion of a strap assembly that is removably attachable to the frame of FIGS. 3 and 4.
Figure 6B:
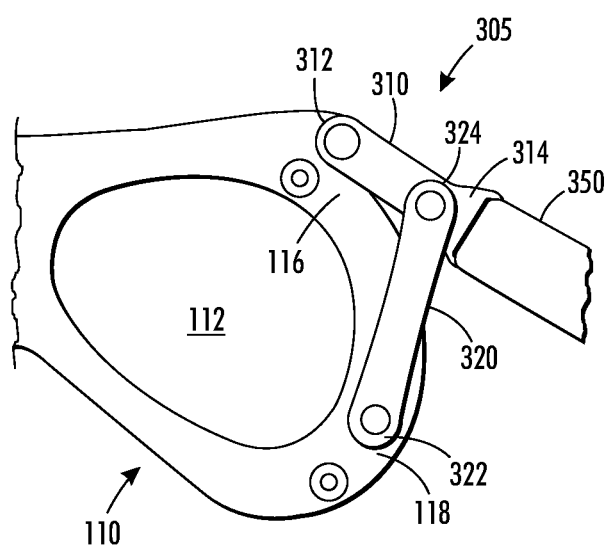
FIG. 6B is an assembled view of the portion of the strap assembly of FIG. 6A, shown attached to the frame of FIGS. 3 and 4.

The gel pack 202 may be removably joined to the frame 100. Referring to FIGS. 5A and 5B, the gel pack 202 is comprised of a casing or pouch 210 containing a gelatinous substance 201. The pouch 210 may be formed by joining a first sheet of material 212 to a second sheet of material 214 at a seal 216 formed at the perimeters of the first and second sheets of material 212 and 214. In other embodiments of the compress system 10 which do not use a gel pack 202, another pack 200 (FIG. 1) may be used, which contains a material other than gel. Other suitable materials have been recited previously herein.

One preferred material for the sheets 212 and 214 of the gel pack 200 is a material comprised of nylon. Nylon materials are preferred for certain thermal and physical properties that will be explained subsequently herein, and for their lack of release of undesired substances when in use, as compared to PVC materials. Although PVC materials are known to be used for the outer envelope materials in gel packs, one disadvantage of commercial PVCs is that they release ("outgas") considerably more substances such as vinyl monomers and additives, especially when heated. It is particularly undesirable to have these substances come in contact with a user's eyes, or be in proximity to a user's nose and mouth where they can be inhaled.

In trying to adapt nylon-based gel packs to the eye region, the Applicants discovered a problem wherein the nylon material was difficult to work with because it did not allow for easy attachment of or to other compress system components via gluing, heat bonding, ultrasonic welding, or other methods. Moreover, industrial sewing also has certain disadvantages in this application. Thus, it proved difficult to attach external items, such as straps and external frames, directly to nylon-based gel packs for the purposes of anatomic fixation. (The Applicants believe that this is why most of the art related to gel packs discusses holding a gel pack onto the body using bags, slings, compression bandages, and similar items in which the nylon-based gel pack is simply inserted into a pocket.)

In contrast to the difficulties involved with attaching components directly to nylon-based gel packs, many known vinyl-based eye gel packs are manufactured with straps attached to the gel packs. Some have straps that are made from the same material as the body of the gel pack, and extend from it. Others have straps that are sewn to side panels of the vinyl that extend from the gel pack. Still others have simple metal-ended elastic strings that are held in place through a hole manufactured into the edge of the vinyl.

In view of the difficulty in bonding components to the nylon gel pack sheet material, the instant compress system is comprised of fasteners to join the gel pack 202 to the frame 100, and to join the strap assembly 300 to the frame 100. The fasteners may be, for example, rivets, screws, grommets, or snaps. To render the gel pack 202 easily removable from the frame 100, snaps are one preferred type of fastener. By using snaps for the gel pack fasteners, the gel pack 202 may be quickly removed from the frame 100 and placed in a hot or cold water bath prior to use. After the gel pack 202 has warmed or cooled to the desired temperature, it may be refastened to the frame 100 and donned by a user.

The Applicants have discovered that snap-type fasteners are advantageous when used with a gel pack 202 that is formed in a particular configuration, for reasons that are explained further below. Referring to FIGS. 5A and 5B, the seal 216 of the pouch 210 of the gel pack 202 is formed around the entire perimeter of the gel pack. The seal 202 may be made by heat sealing, wherein a heated die is applied to the perimeter so as to fuse the mated edges of the sheets 212 and 214 to each other. Around most of the perimeter, the seal 216 extends inwardly a uniform distance from the perimeter edge 217. However, at a plurality of locations around the perimeter, there are provided inward indentations in the seal that are provided with holes for receiving fasteners. In the gel pack embodiment 202 depicted in FIG. 5A, two upper inward indentations 218 and 220, and two lower inward indentations 222 and 224 are provided. Through holes 228, 230, 232, and 234 are provided in the respective indentations 218-224 for receiving a part of a fastener therethrough. The indentations 218-224 may have an inward arcuate profile, i.e. a portion of an arc of a circle, such as the circle 229 shown partially in dotted line format.

By way of illustration, and not limitation, in one embodiment a gel pack 202 may be fabricated having a width of about 10 inches (255 mm), and a height of about four and one-half inches (115 mm). The exemplary gel pack may have a primary seal width 219 along most of the perimeter of about 0.2 inches (5 mm). The indentations 218-224 may have an inward arcuate profile of a circle of about 0.4 inches (10 mm) in diameter. The through holes may be about 0.08 inches (2 mm) in diameter. Both of the sheets 212 and 214 of the gel pack envelope or pouch 210 may be die cut, with piece 214 being sized larger than piece 212 so that it can form the volume of the pouch 210 that contains the gel 201. Alternatively both pieces can be sized so that they form equal portions of the pouch 201. The pieces 212 and 214 may be placed in a heat sealing fixture and sealed around most of the perimeter except for an unsealed location allowing entry of a filling nozzle; gel 201 may then be introduced between the pieces using the filling nozzle, and finally the two pieces may be heat-sealed together in the previously-unsealed location to form the final gel-filled gel pack 202 as shown in FIGS. 5A and 5B.

In the general configuration depicted in FIGS. 5A and 5B, (although dimensions may vary from the example provided above), the Applicants have discovered that when using snap fasteners, the footprint of the snap attachment may be quite small in diameter, relative to the security that it provides. Moreover, the size of the through hole for receiving a portion of the snap may be quite small. For example, a typical industrial snap with a 10 millimeter cap will require making a die cut hole (e.g. holes 228-234) of only around 2 millimeters in diameter. The size of the male or female snap component fitted to an indentation in the seal 216 may be about 9.4 mm. When such a male or female snap component is centered over a die cut hole, it will still only contact the heat-sealed periphery of the gel pack. In other words, it will lie completely within the area defined by the total indentation in the seal (e.g. indentation areas 218-224). The fitted snap component thus remains firmly attached to, but does not substantially deform or otherwise damage, the gel-containing portion of the gel pack. Stable attachment is thus possible within even the narrow heat-sealed periphery of the gel pack 202, and thus it is possible to obtain a relatively narrow seal with the snap system. A relatively narrow edge seal is preferred in applications in which users may elect to use the gel pack directly against their skin. This is because gel packs with wider edge seals can, over time, produce greater amounts of edge curling, resulting in a "crinkly edge" which, if extensively present, can be uncomfortable when the curled edge comes into contact with the face of a user.

In contrast, joining the gel pack 202 to the frame 100 by industrial sewing, heat-bonding, or ultrasonic welding would require a greater joining surface area in order to attain a similar degree of safe and stable strength as a snap. Additionally, whereas in a snap-based system the exact locations of attachment are determined by the mold and die cut processes, systems relying on other means of attachment would rely on a human laborer to choose a location for sewing, heat-bonding, or otherwise affixing gel pack 202 to frame 100. The same principle holds true when considering other items that can be attached to a gel pack, such as the use (in other embodiments) of straps directly attached to a gel pack. The use of snaps is especially beneficial in the instant compress system 10, because it is desirable that such attachment locations be made with high degrees of accuracy (in some embodiments, to fractions of a millimeter), for reasons that will be explained subsequently. Additionally, using snaps or snap-like attachments such as rivets, grommets, posts, and the like rather than a sewn, heat-bonded, friction-secured, or other forms of frame or strap attachments, significantly reduces the possibility of damage to the gel pack pouch 210 or seal 216 during the compress system 10 manufacturing process. For example, a worker using a snap-press to fit a snap component to the gel pack 202 is much less likely to cause damage to the gel pack 202 than a worker implementing these other means of attachment.

Additionally, snaps or snap-like attachments (such as rivets and the like) may also be used to attach other devices to the gel pack 202. Such devices could include, for example, edge members, such as flat plastic components used to cover or to attach to a portion of the sealed lateral edge regions 236 and 238 of gel pack 202, rather than to the top edge of gel pack 202. Such edge members, for example, could be used as further means of attachment of other devices, such as head straps. Thus, for example, one or more plastic edge members could be temporarily or permanently affixed to one or both side portions of gel pack 202, and one or more head straps could further be temporarily or permanently affixed to the plastic edge members, as disclosed in the aforementioned commonly owned PCT Application No. PCT/US2009/044327. The method of affixing such side edge members to a gel pack could be similar or identical to the method of affixing snap members 242-272 to the gel pack 202 described above.

Figures 10, 11:
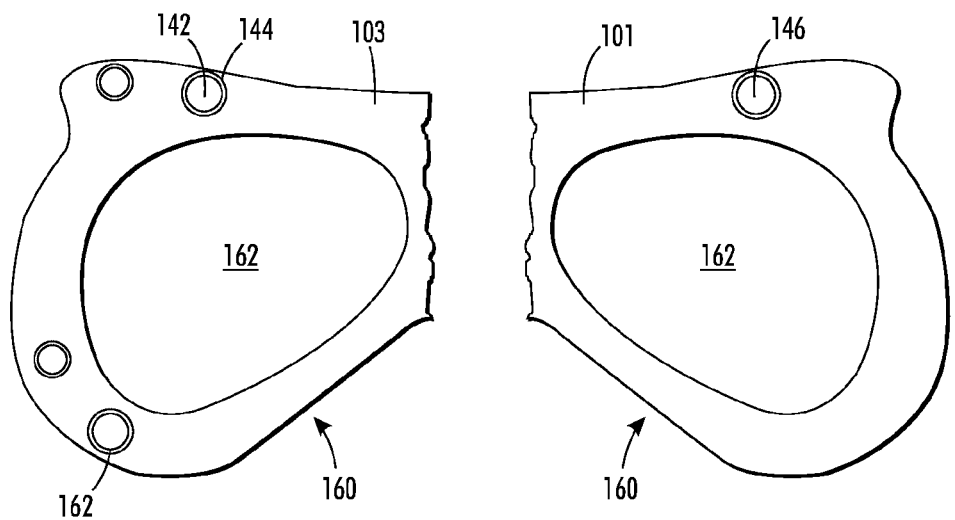
FIG. 10 is detailed rear view of a frame region of a frame for supporting a gel pack against the eye region of a user, showing a recessed snap fastener formed thereupon.
FIG. 11 is detailed front view of the frame region of the frame of FIG. 10, showing a protrusion thereupon provided opposite the recessed snap fastener.

Referring again to FIGS. 2 and 4, in the embodiment depicted therein, first and second upper snap assemblies 240 and 250, and first and second lower snap assemblies 260 and 270 removably join the gel pack 202 to the frame 100. (In FIG. 4, although only the outline 203 of the gel pack 202 is shown, the snap assemblies 240-270 are also shown.) Referring also to FIG. 10, a first upper snap piece 242 joins the gel pack 202 to a first mating upper snap piece 142 on the inner side of the second frame section 160, through the hole 228 in the first inward indentation 218 in the seal 216. In like manner, a second upper snap piece 252 joins the gel pack 202 to a first mating upper fastener (not shown) on the inner side of the first frame section 160, through the hole 230 in the second inward indentation 220 in the seal 216. A first lower snap piece 262 joins the gel pack 202 to a first mating lower snap piece 162 on the inner side of the second frame section 160, through the hole 232 in the third inward indentation 222 in the seal 216. In like manner, a second lower snap piece 272 joins the gel pack 202 to a first mating lower snap piece (not shown) on the inner side of the first frame section 110, through the hole 234 in a fourth inward indentation 224 in the seal 216.

The snap pieces 242, 252, 262, and 272 are joined to the gel pack 202 such that they sandwich the peripheral edge seal 216 of the envelope material, with the smooth cap of the snap pieces 242-272 facing rearwardly, i.e. toward the user. The details of the attachment of one configuration of snap piece are as follows. The snap piece such as piece 242 may be provided in two pieces (not shown): a cap-and-post piece, and a stud-or-socket (male-or-female) piece. The post from the cap-and-post piece is disposed through the hole 228 in the seal 216 of the gel pack. 202. The other piece (in embodiment depicted in FIG. 14, a stud, or male, piece) is placed onto the post, with the post going through the central hole of the stud piece. A snap-press tool (not shown) is then used to flatten the post onto the center holding-portion of the stud element to keep it secure on the gel pack 202. The use of a cap-and-post type snap piece is beneficial because only a small hole is needed through the seal 216 of the gel pack. Accordingly, only small indentations 218-224 are needed in the seal 216 to receive the snap pieces.

In choosing the locations of the snap pieces on the gel pack 202 and frame 100, a balance may be achieved between the security and stability of the gel pack 202, and the user's ability to use the compress system 10 without feeling the snaps press into the head or face. A top-edge attachment is beneficial in that when used in the upright position, it allows the gel pack 202 to hang down without stretching it horizontally to any substantial degree or causing horizontal creases or folds in the surface of the gel pack.

The Applicants have discovered that the snap assemblies 240 and 250 that are positioned along the top edge of the frame 100 press uncomfortably against the foreheads of some users where the frame 100 drapes over the convexity of the forehead. To address this problem, the snap attachments along the top edge of the frame may be recessed into the frame 100, so that the snap pieces fitted to the gel pack are located away from the user's head when in use. Referring in particular to FIG. 10, snap piece 142 is disposed in a recess 144 that is provided on the rear side (user's side) 103 of frame portion 160 of the frame 100. In like manner, the corresponding snap piece on the rear side 103 of frame portion 110 is also disposed in a recess. To maintain the thickness of the frame 100 at the recess 144 (and the recess of the frame portion 110), the frame may have a protrusion 146 on the front side of the frame 100. The snap pieces such as piece 142 may be formed integrally as part of the frame 100, which may be made by molding.

The use of snaps to make the gel pack 202 easily removable from the frame 100 may create a risk that users will simply pull the gel pack 202 off the frame in one tugging motion, rather than unsnapping one snap at a time. Pulling the gel pack in this manner risks weakening or tearing the gel pack 202 if a snap holds firm, and sufficient damage to the gel pack would render it useless. To address this problem, the gel pack 202 may be provided with snap pieces 242, 252 262, and 272 with larger-diameter caps. Such large diameter capped snap pieces become unsnapped more easily when a general dislodging force is applied to the material that the cap side of the snap is attached to. Without wishing to be bound to any particular theory, the Applicants believe that the force of the gel pack pulling on the "longer lever" of the larger cap diameter translates into a greater "unsnapping force" at the center of the snap. (This is opposite the desired result in most snap-fastened applications, such as clothing, in which continued closure is desirable until the user specifically opens the snap. A larger cap that makes it very easy to dislodge a clothing snap would lead to frequent inappropriate unfastenings of the article of clothing.) By way of example, in one embodiment, the snap pieces 242, 252 262, and 272 were provided with caps having a diameter of about 16 mm, despite having all other snap components (post, stud component, and socket component) sized for a standard industrial snap with a cap diameter of 10 mm. By extension, any snap system in which the cap diameter significantly exceeded the standard diameter that would be expected based on the dimensions of the snap body pieces would confer the advantage of easy removal described above.

The Applicants have discovered by further experimentation and testing that a larger range of potential cap diameters may prove advantageous for a given snap or stud diameter. For example, given the above example of a snap set with a standard cap diameter of 10 mm that is paired with a stud or socket of standard size, even a cap of 10.5 or 11 mm in diameter may be easier to dislodge than a cap that is 10 mm in diameter. Alternately, rather than having a larger cap, a washer or collar placed under an existing cap could achieve similar results.

Without wishing to be bound to any particular theory, the Applicants believe that the key to effective results with this system is to optimize the ratio between the cap diameter and the diameter of the stud or socket to which the cap is paired. The diameter of this stud or socket attachment mechanism is what gives strength to the attachment of the gel pack snap component to the frame snap component, and the cap diameter (or washer or collar diameter) creates the lever-type force that dislodges the stud or socket from the cap. For example, in one standard commercial snap set, a cap of 10.4 mm diameter was paired with a stud of 9.4 mm diameter, yielding a cap-to-stud diameter ratio of 1.11. If the cap diameter was increased by 0.5 mm to 10.9 mm in this system, this would create a cap-to-stud diameter ratio of 1.15. Similarly, an increase in the cap diameter to 11.3 mm would create a cap-to-stud diameter ratio of 1.20. Thus in one embodiment, a cap-to-stud or cap-to-socket diameter ratio of at least 1.15 is preferred. In another embodiment a ratio of at least 1.20 is preferred. In yet another embodiment, a ratio of at least 1.25 is preferred. In yet another embodiment a ratio of at least 1.30 is preferred.

Although a variety of snap materials may be suitable, the materials used for snaps may be selected based on a tradeoff between a need for a soft material (so that if the user wears the unit and feels the cap-heads against his/her skin, he/she will not be uncomfortable), and a need for durability. In one embodiment in which the frame 100 is made out of LDPE, and in which the frame snap pieces are integrally formed as a part of the frame 100, the mating gel pack snap pieces may be made of a harder plastic, such as e.g., HDPE. Prototypes of these snap pairings have been made and found to have no breakdown in use with testing of over 100 repetitions of snapping on and off.

The Applicants have discovered that an unexpected advantage of using snaps to join the gel pack 202 to the frame 100 over joining by adhesives or other means is that the very small area of fixation involved when using snaps allows significantly more "play" in the gel pack 202 when compared to methods involving larger areas of fixation. In that manner, the gel pack 202 may deform more naturally over the anatomical features of the user. In contrast, using other means of attachment such as gluing or adhesives, heat bonding, industrial sewing, and the like, would require larger fixation areas in order to achieve a similar strength and stability of holding-power. The larger area of attachment required would affix substantial areas of the peripheral seal 216 of gel pack 202 to the frame 100, thereby not allowing sufficient "play" or movement in the gel pack and instead leading to a more tightly adherent and taut gel pack surface that was less-conformable and less comfortable to the user.

The Applicants have also found that the amount of play can be improved to produce a more "soft" and conforming feeling of the compress system 10 to the user by unsnapping the lower snaps 260 and 270 of the gel pack 202, and simply relying on the upper snaps 240 and 250 to hold the gel pack 202 along the top edge of the frame 100. However, it is desirable for the sake of stable attachment to have the gel pack 202 attached to the frame 100 at all four points of snaps 240, 250, 260, and 270. To address the problem of having increased play in the gel pack 202 when in use, while still having the gel pack 202 attached at four points, the gel pack 202 may be configured such that the distance between the third inward indentation 222 in the seal 216 and the fourth inward indentation 224 in the seal 216 when the gel pack 202 is not joined to the frame 100 may be greater than the distance between the first mating lower fastener on the inner side of the first frame section 110 and the first mating lower fastener 162 on the inner side of the second frame section 160. In that manner, when the gel pack 202 is joined to the frame 100 by the snap pieces 262 and 272 which are located at the indentations in the seal, a relaxed fit of the gel pack 202 is provided, such that it is not taut across the eyes of the user, thereby providing greater comfort to the user and better conformance of the gel pack 202 to the eyes.

Figure 9:
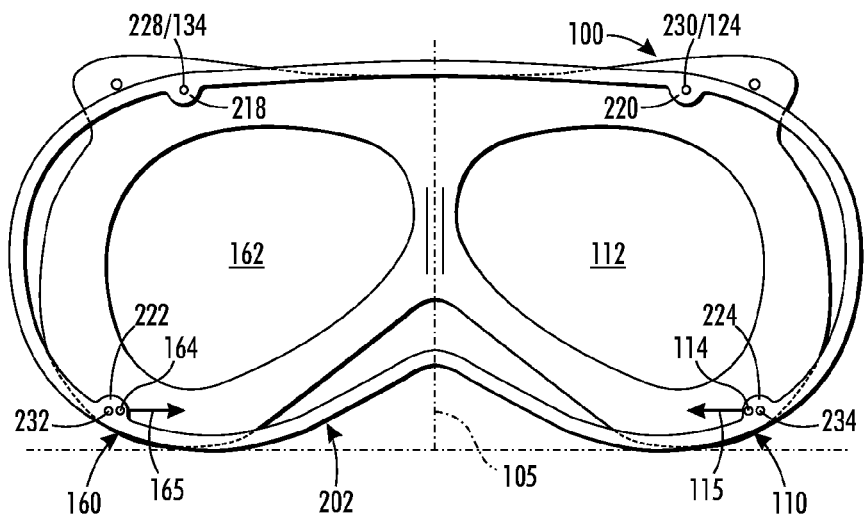
FIG. 9 is a schematic illustration of the dimensional and geometrical relationships of a frame and a gel pack in one embodiment of the Applicants' thermal compress system.

This may be better understood with reference to FIG. 9, which is a schematic illustration, viewed from the rear, of the outline of the gel pack 202 superimposed on a modified schematic outline of frame 100 in which molded snap receptacles as such as 142 and 162 (FIG. 10) are replaced by diecut holes such as 124 and 114, and in which the diecut holes are concentric with the positions of the corresponding snap receptacles. This illustration thereby depicts the dimensional and geometrical relationships between the gel pack and the frame. It can be seen that the holes 228 and 230 in respective upper indentations 218 and 220 in seal 216 are concentrically aligned with the corresponding holes 134 and 124 in frame 100, and thus only one hole can be seen at each location in FIG. 9. Thus in the assembly of the compress system 10, the snap pieces 240 and 250 on the gel pack 202 align directly with the mating snap pieces on the frame 100.

In contrast, it can also be seen that the holes 114 and 164, which are concentric with the corresponding frame attachments used for fastening the lower snaps to the frame 100, are located inwardly from the holes 232 and 234 which locate the snap pieces 262 and 272 on the gel pack 202. This displaces the location of the lower snap positions on the frame 100 inwardly toward center line 105, relative to the snap positions on the gel pack 202, when the gel pack 202 is in a free position unfastened to the frame 100. When the gel pack 202 is fastened to the frame 100, the snap pieces 262 and 272 are displaced inwardly as indicated by arrows 115 and 165. This renders the gel pack 202 less taut than it otherwise would be if the lower snaps of the gel pack 202 in its free state were directly aligned with the lower snaps of the frame 100, and the less-taut configuration in turn provides a better and more comfortable fit of the gel pack 202 to the eye region of the user when the compress system 10 is donned by the user. In the embodiment of the gel pack 202 having the dimensions previously recited with reference to FIGS. 5A and 5B, the amount of displacement of each lower snap on the gel pack 202 was about 3.75 mm centrally relative to the position of its corresponding mating snap on the frame 100.

Referring again to FIGS. 5A and 5B, there are numerous plastic film or sheet materials that may be suitable for joining together to form a gel pack envelope or pouch 210. As indicated previously, the films may be comprised of nylon, also known as polyamide. The film may be a two-layer structure having a nylon-based outer layer and an LLDPE (linear low-density polyethylene) inner layer. The "nylon-based" outer layer confers barrier protection without being too stiff. It prevents diffusion through the film and evaporation of any volatile constituent of the gel contents, adds strength to the heat seal, and also confers a tougher outer component that prevents fingernail snags and other causes of incidental damage to the gel pack surface that could lead to leakage of gel. The LLDPE layer confers extra thickness and also allows for a controlled heat seal using conventional heat sealing methods.

In certain embodiments, the "nylon-based" layer may consist essentially of nylon, or it may consist essentially of biaxially-oriented nylon, also known as BOPA, or biaxially-oriented polyamide. Biaxial orientation is a process that stretches the film twice, in two orthogonal directions. This produces an exceptionally clear and somewhat stiffer film that may also impart improved strength and resistance to incidental damage. Thus, BOPA may be preferred over nylon for gel packs that are going to be primarily used in a heated state. In such circumstances, the increased strength of the nylon may be more important than the pliability of the film, which occurs regardless because of the heat present. Pliability may also be less important with a heated gel pack, because users will often use the compress system 10 with a moist cushioning sheet disposed between the gel pack 202 and the eye region.

In other embodiments, when the gel pack 202 is to be used in a cooled state, the films of the gel pack 202 may be selected to have greater softness and flexibility. In such circumstances, it would be more acceptable to have a soft and pliant film, even if such film were potentially more easily damaged. This is because there would be no risk of hot gel contacting the face of a user by a leak in the gel pack 202. In such gel packs, one exemplary material that may be used is ethylene vinyl acetate (EVA), which may be added to the film (and perhaps more particularly to the nylon layer) in order to improve the softness of the feel of the gel pack film, as well as to improve certain barrier characteristics.

For two-layered film structures, the selected film components may be either coextruded or laminated to achieve the final single-ply product, from which two sheets are then sealed together form the gel pack 202. In some embodiments, lamination may be preferred, because it confers the benefit of preparing the two finished materials separately before they are fused together. This has advantages because "internal printing" may be performed on the nylon layer, which allows permanent printing that is contained within the final film, and thus will not fade with use. This may be beneficial because permanent instructions for use may be desirable to be printed on the gel pack 202. It also allows permanent decorative designs to be printed on the gel pack 202.

The thickness of the film may also be chosen in a manner so as to determine the strength and pliability thereof, with a thinner material conferring a greater degree of pliability. In general, laminated films (e.g., made of a layer of LLDPE laminated to a layer of nylon), measuring a total thickness no greater than 4.0 mil (0.004"), were preferred. Laminated films measuring 3.0 mil (0.003") thick had an even softer feel and were thus even more preferable, and laminated nylon-LLDPE film at 2.5 mil (0.0025") were softer yet and thus even more preferable. Though softer, the thinner films retained good protection and seal strength. Among laminated nylon-LLDPE films measuring 2.5 mil (0.0025"), having the nylon layer measure between around 0.4 mil (0.0004") and 0.8 mil (0.0008"), so that the LLDPE layer measured around 2.1 mil (0.0021") to 1.7 mil (0.0017"), was generally preferred.

In another embodiment of the Applicants' compress system, the system 10 includes a frame, a gel pack, and a strap assembly. This is best understood with reference to FIGS. 6A-8, in addition to FIGS. 1-4. Proximate to the first frame section 110 of the frame 100, the strap assembly 300 is comprised of a first V-subassembly 305 comprising a first inelastic upper member 310 and a first elastic lower member 320. The first inelastic upper member 310 is pivotably joined at an inner end 312 thereof to an upper lateral portion 116 of the first frame section 110. The first elastic lower member 320 is pivotably joined at an inner end 322 thereof to a lower lateral portion 118 of the first frame section 110, and is joined at an outer end 324 thereof to the outer end 314 of the first inelastic member 310.

In like manner, proximate to the second frame section 160 of the frame 100, the strap assembly 300 is comprised of a second V-subassembly 355 comprised of a second inelastic upper member 360 and a second elastic lower member 370. The second inelastic upper member 360 is pivotably joined at an inner end 362 thereof to an upper lateral portion 166 of the second frame section 160. The second elastic lower member 370 is pivotably joined at an inner end 372 thereof to a lower lateral portion 168 of the second frame section 160 and is joined at an outer end 374 thereof to the outer end 364 of the second inelastic member 360.

A connecting strap 350 joins to the slot 316 in the outer end 314 of the first inelastic member 310 and the slot 366 in the outer end 364 of the second inelastic member 360. A complete strap assembly 300 is thus provided to secure the compress system 10 to the head 2 and eye region of the user.

In the first V-subassembly 305, snaps may be used to pivotably join the first inelastic member 310 to the frame portion 116, and to pivotably join the second elastic member 320 to the frame portion 118, and to pivotably join the second elastic member 320 to the first inelastic member 310. (It is noted that in FIG. 4, the inner ends 322 and 372 of the first and second elastic members 320 and 370 are not shown snapped to the respective frame sections 110 and 160.) A slot 316 may be provided in the outer end 312 of the first inelastic member 310, through which the connecting strap 350 may be threaded and joined onto itself, thereby joining the connecting strap 350 to the first inelastic member 310. In the second V-subassembly 355, snaps and a slot may be used in a similar manner.

Figure 7:
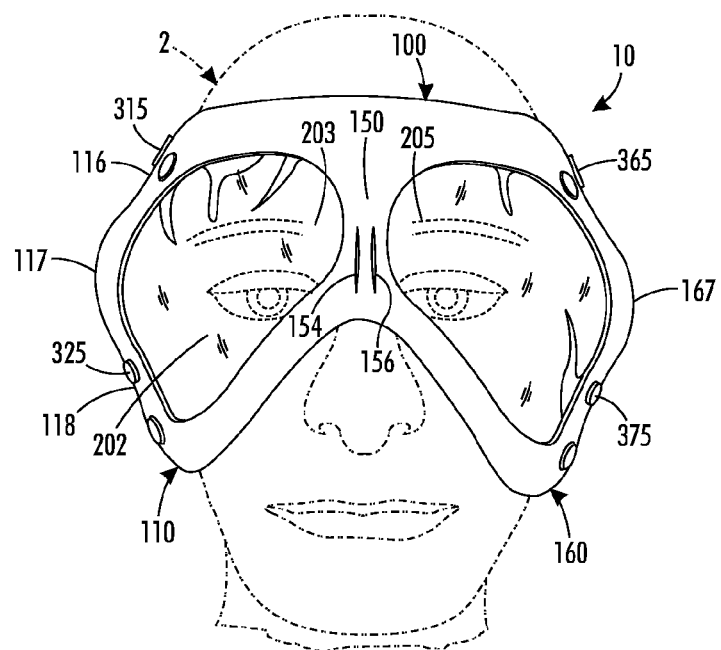
FIG. 7 is a front view of the thermal compress system of FIG. 1, shown fitted to the eye region of a user.
Figure 8:
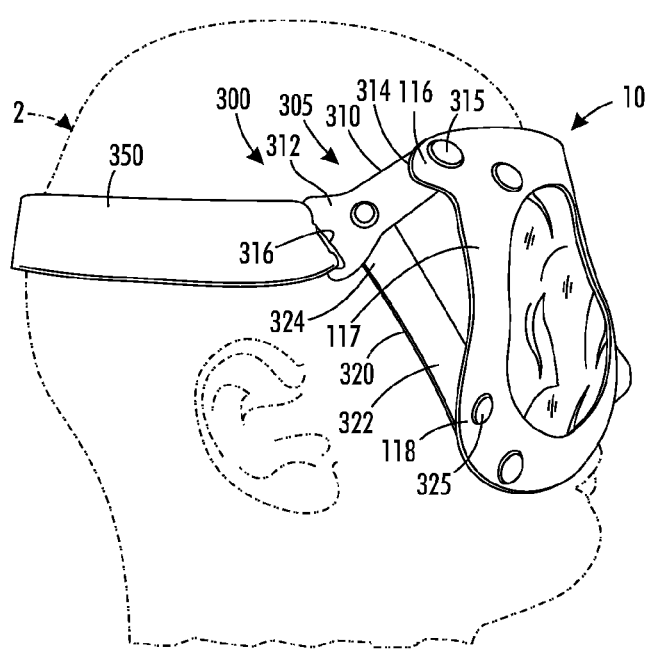
FIG. 8 is a side view of the thermal compress system of FIG. 1, shown fitted to the eye region of a user.

The Applicants have discovered that by configuring the V-subassembly 305 and the V-subassembly 355 in the foregoing manner, the middle lateral portion 117 of the frame section 110 between the fastener 315 and the fastener 325, and the middle lateral portion 167 of the frame section 160 between the fastener 365 and the fastener 375 is pulled away from the user's eye region when the connecting strap 350 is placed around the user's head to hold the frame 100 and gel pack 202 (optionally with a sheet, not shown) against the eye region of the user 2. Said another way, bends are created in the middle lateral portion 117 of the frame section 110 between the fastener 315 and the fastener 325, and the middle lateral portion 167 of the frame section 160 between the fastener 365 and the fastener 375, which is best seen in FIGS. 7 and 8. This causes a reduction in the pressure of the gel pack 202 directly against the eyes of the user, while more pressure is applied to the regions above and below the eyes of the user (e.g., the periphery of the user's eye region). The reduction in direct pressure upon the eyes, and the corresponding snug feeling of the gel pack against the upper cheek, is more comfortable to the user.

Without wishing to be bound to any particular theory, the Applicants believe that by providing the upper members 310 and 360 of the V-strap assemblies 305 and 355 as inelastic rigid members, they act as act as levers to more forcibly pull the respective elastic members 320 and 370 upwardly, thereby inducing more pronounced bends 117 and 167 in the frame 100. The use of elastic materials in upper members 320 and 370 did not produce as significant or effective a result in this regard.

In some embodiments, the upper members 310 and 360 may be made of a plastic such as nylon, polypropylene, high-density polyethylene, or low-density polyethylene. The thickness of such materials would tend to be roughly equivalent to the thickness of similar materials used in the external frame. Without wishing to be bound to any particular theory, the Applicants believe that because the torque applied upon the body of the inelastic member by the elastic member is perpendicular to the flat plane of the inelastic member, the inelastic member resists bending, and thus even the use of less-rigid materials in the inelastic member, such as low-density polyethylene, was found to achieve excellent leverage force and to induce significant bending of the frame as described above. Thus, inelastic upper members may be made of any material that substantially resists bending when a force is applied which is perpendicular to the flat plane of the inelastic member. Such materials may include, for example, metals, paper products, stiffened foams, and other materials.

Figure 19A:
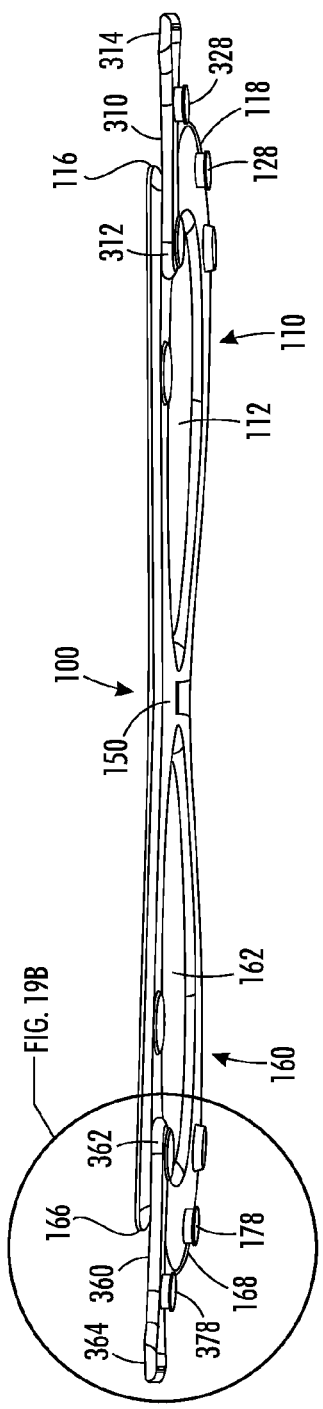
FIG. 19A is an oblique top view of the frame of FIG. 3 showing fasteners for attaching portions of a strap assembly to the frame.
Figure 19B:
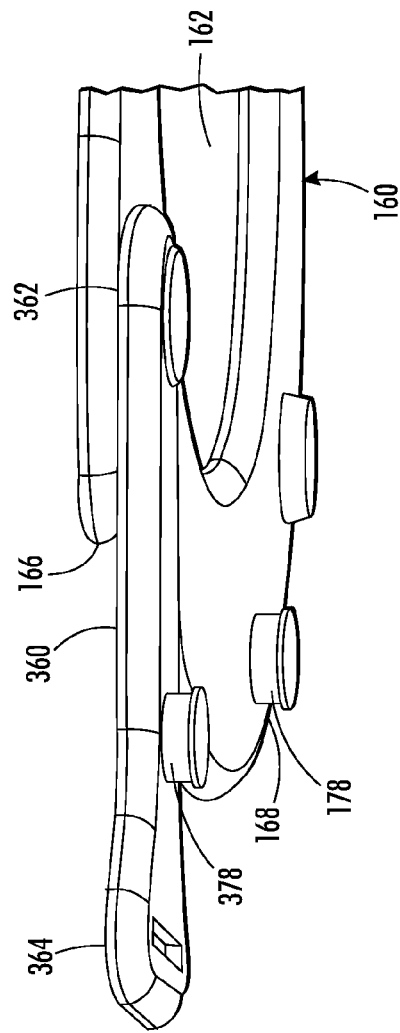
FIG. 19B is a detailed view of the portion contained within the circle 19B of FIG. 19A.

The elastic lower members may be made of an elastomer, such as silicone rubber. "Mushroom-shaped" posts may be used as the fasteners to attach the upper members 310 and 360 to the frame 100, and to attach the lower members 320 and 370 to the frame 100 and to the upper members 310 and 360. Referring in particular to FIGS. 4, 19A and 19B, a first mushroom shaped post 328 pivotably joins the outer end 324 of first elastic upper member 320 to the outer end 314 of the first inelastic member 310, and a second mushroom shaped post 128 pivotably joins the inner end 322 of first elastic upper member 320 to the lower lateral portion 118 of the first frame section 110. In like manner, a first mushroom shaped post 378 pivotably joins the outer end 374 of second elastic upper member 370 to the outer end 364 of the second inelastic member 360, and a second mushroom shaped post 178 pivotably joins the inner end 372 of second elastic upper member 370 to the lower lateral portion 168 of the second frame section 160.

Such mushroom-shaped posts, which may be located at fixed positions on certain components and can, for example, be injection-molded at those locations, allow for easy assembly of components, since a molded or die-cut hole in a second component can be pressed down over the mushroom-shaped post on the first component, so that the mushroom-shaped top of the post slightly deforms and then returns to its shape, thereby holding the second component in place. Such mushroom-shaped posts also allow full pivotable attachability of such components to one another. These posts are thus unexpectedly advantageous in the area of support systems for body compress assemblies, because they allow for a high degree of both convenience and precision in the design for manufacture, and also allow for pivotable attachability of subassembly components, which are important features of body compress assemblies relying on calculated and adjustable deformation in order to exert forces in desired directions.

The connecting strap may be made of polymer webbing, such as e.g., braided elastic, soft elastic, or knit elastic. In one embodiment, a knit elastic made of polyester and latex was used, having a width of about one inch. The webbing may be joined to the respective upper members 310 and 360 by threading it through slots provided therein, and then sewing the webbing onto itself. Alternatively, the ends of the connecting strap 350 may be provided with hook-and-loop fastening material, so that the connecting strap 350 is made removable from the v-strap assemblies 305 and 355. In turn, connecting strap 350 may either be a single continuous strap, or may be divided into two separate ends, each of which connects to the other with a hook-and-loop fastening material, allowing adjustable fastening around the back of the user's head 2.

Figure 12:
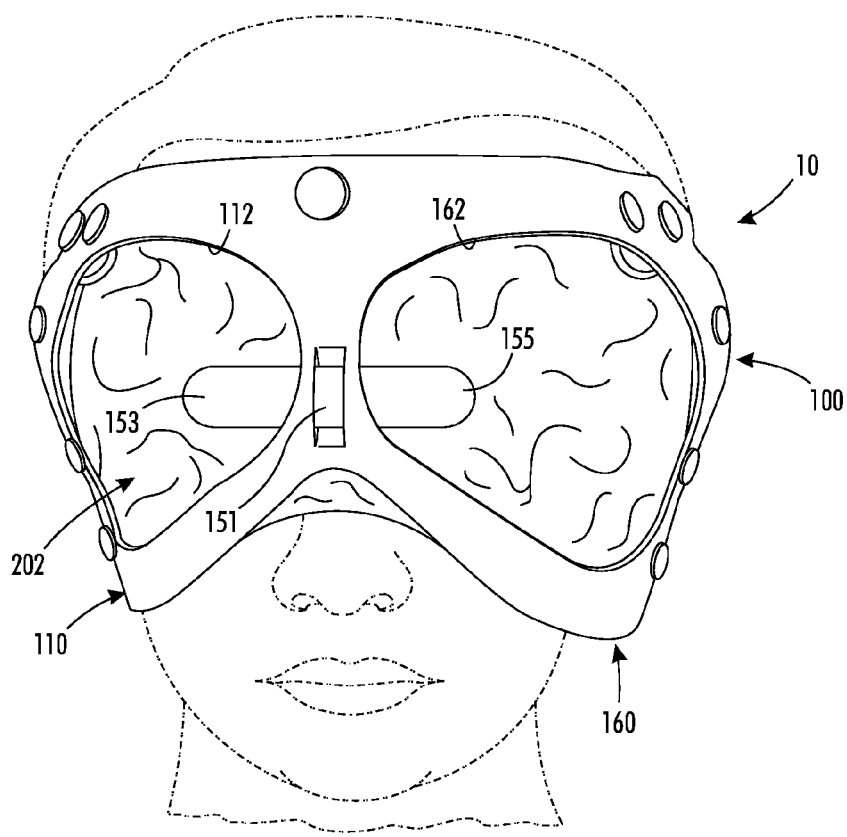
FIG. 12 is a front view of a thermal compress system similar to that shown in FIG. 7, but further comprising a gel impressor as shown in FIGS. 1 and 2
Figure 13:
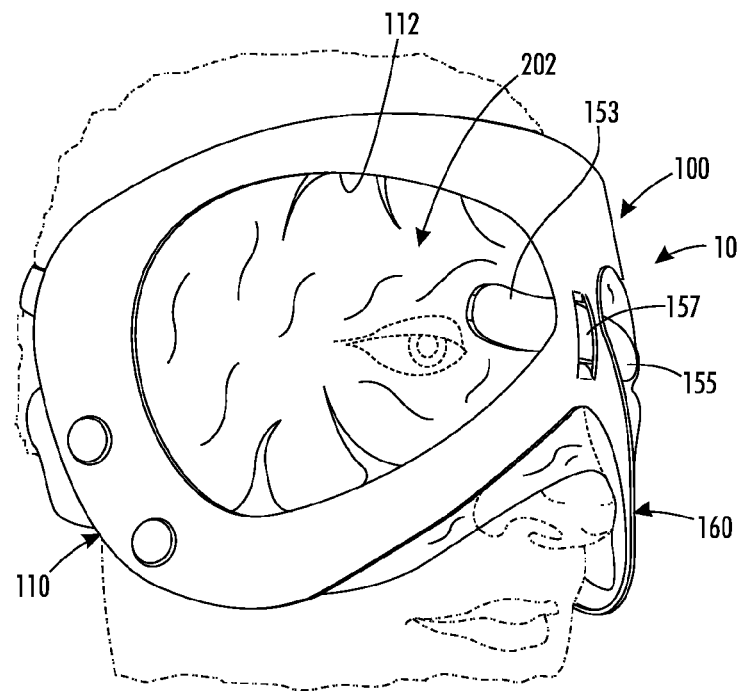
FIG. 13 is a lower oblique view of the thermal compress system of FIG. 12, shown with the gel impressor in a flat, undeployed position.
Figure 14:
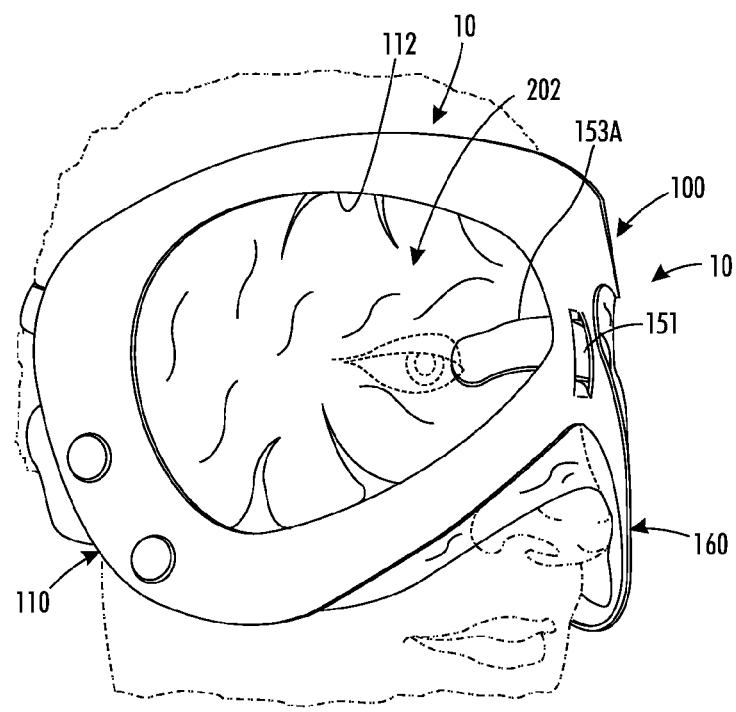
FIG. 14 is a lower oblique view of the thermal compress system of FIG. 12, shown with the gel impressor in an inwardly bent, deployed position.
Figure 15:
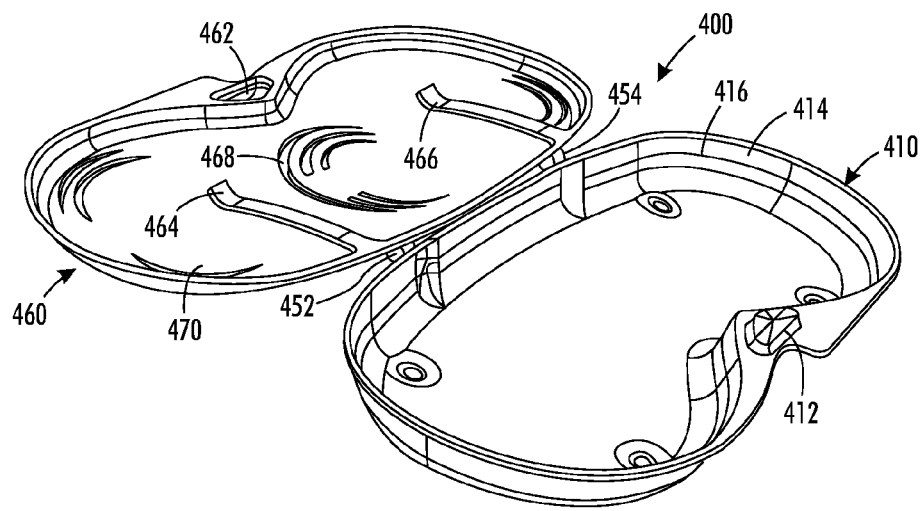
FIG. 15 is a perspective view of a storage case for a thermal compress system, the case depicted empty and in the fully open position.
Figure 16:
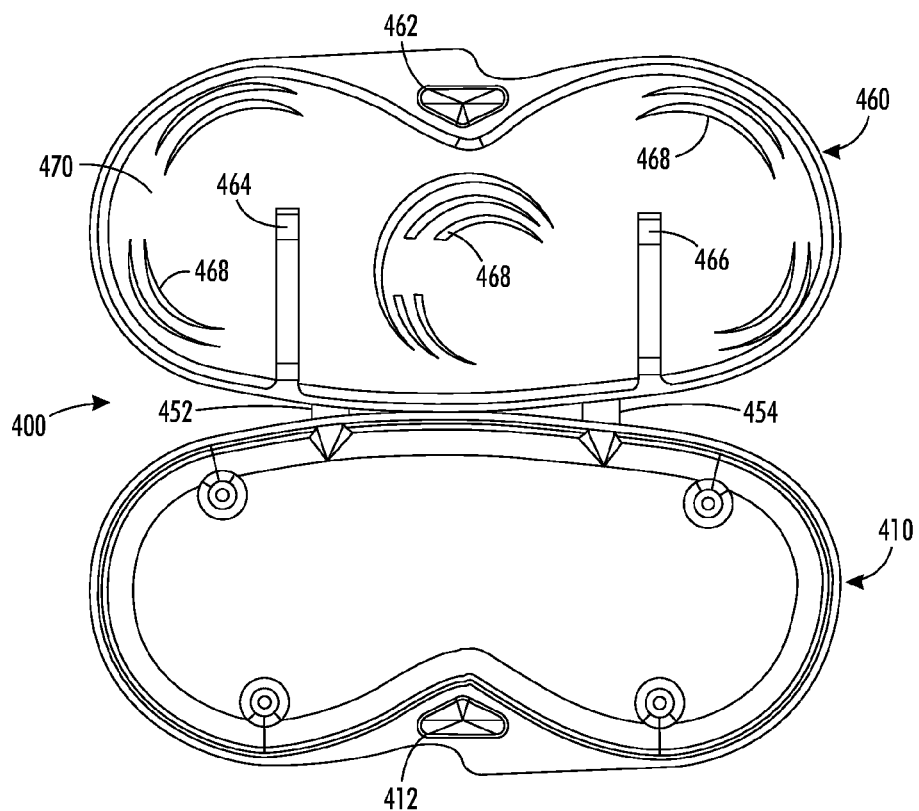
FIG. 16 is a plan view of the storage case of FIG. 15.

In another embodiment of the Applicants' compress system, the system 10 includes a frame, a gel pack, and a gel impressor joined to and extending laterally across the central bridge 150 of the frame 100. This is best understood with reference to FIGS. 12-14, in addition to FIGS. 1-4. Referring first to FIGS. 12-14, the gel impressor 151 is comprised of a deformable plate of material including a first portion 153 extending over the aperture 112 in the first frame section 110, and second portion 155 extending over an aperture 162 in the second frame section 160. The first portion 153 is inwardly deformable so as to contact a first portion 203 (see also FIG. 7) of the gel pack 202 and displace it toward the nasal corner of the first eye (the nasal canthus) of the user, and the second portion 155 is inwardly deformable so as to contact a second portion 205 (see also FIG. 7) of the gel pack 202 and displace it toward the nasal corner of the second eye of the user. This is best understood with reference to FIG. 14, in which it can be seen that the bent first portion 153A is displacing the first portion 153 of the gel pack 202 toward the nasal corner of the first eye of the user.

In that manner, the gel impressor 151 can provide a hands-free option for creating selected indentation in certain areas of the gelatinous substance of the gel pack. The gel impressor 151 may be longer or shorter than depicted in FIGS. 12-14. The gel impressor 151 may be made of a flexible and bendable material that retains the shape to which it is bent. Metals such as aluminum or steel may be suitable. In other embodiments, the gel impressor may be made of plastic and/or any other material that can press the gel pack 202 against the nasal corners of each eye. In some embodiments, the gel impressor may have a thickness of between about 0.008 and about 0.030 inches thick. In one exemplary embodiment, a gel impressor was made from a piece of sheet aluminum of approximately 0.020 inches thick, and approximately 2½" wide by ½" high.

As shown in FIGS. 7 and 12-14, the frame 100 may be provided with a pair of slots 154 and 156 formed in the bridge thereof. To fit the gel impressor 151 to the frame 100, the gel impressor 151 may simply be slid through the slots 154 and 156 as shown in FIGS. 12-14. In another embodiment, the frame 100 may be provided with a fixture 157 that is joined to the bridge 150 of the frame 100, or integrally molded as part of the frame 100. The fixture is provided with slots, through which the gel impressor 151 may be slid. The slots are dimensioned so as to provide a mild interference fit with the gel impressor 151 at its chosen thickness. A more secure fit of the gel impressor 151 may be obtained by coating it with a compliant polymer or rubber coating, such as PLASTI DIP® made and sold by Plasti Dip International of Blaine, Minn. Alternatively, a thin layer of adhesive-backed foam may be applied to one or both sides of the gel impressor 151. Such a coating or foam has the added benefit of covering any sharp edges of the gel impressor, which could otherwise cut into the gel pack film.

Although the gel impressor 151 is depicted as being used to apply pressure over the nasal canthal regions of the user's eye region, such a gel impressor 151 is not limited solely to this use. The instant compress system 10 may be configured to apply to other anatomic regions, including one or more gel impressors 151 to dispose a gel pack 202 toward specific location of those regions.

The instant compress system 10 disclosed herein may further include a fabric sheet of material which is disposed between the gel pack 202 and the body part of the user being treated. The use of fabric sheet material, and non-woven fabric sheet material is discussed in detail in commonly owned PCT Application No. PCT/US2009/044327. The applicants have further discovered that it is desirable that the fabric sheet material be a hydrophilic material. It is preferable that the sheet material be capable of absorbing at least about 4 cubic centimeters of water per gram of sheet material, and more preferably at least about 8 cc of water per gram of sheet material, and even more preferably at least about 12 cc of water per gram of sheet material. This is in contrast to the applications of fabric sheets used with gel packs that are known to the Applicants, in which hydrophobic fabric materials are used specifically to keep such materials in contact with a user's body part dry.

It is also desirable that the non-woven sheet material be somewhat "plush," i.e. relatively thick and soft, yet not so thick that it blocks the thermal transmission from the gel pack. It is preferable that the sheet material have a weight of at least about 40 grams per square meter (gsm), and more preferably at least about 50 gsm, and even more preferably at least about 60 gsm. In one exemplary embodiment, a non-woven sheet material was used, which was cut in a pattern slightly larger than the perimeter of the gel pack 202 shown in FIG. 5A. The non-woven sheet material was made from spun-lace 60 gsm material.

The non-woven sheets may be selected based upon their ability to absorb and hold water or other aqueous liquids, so that such liquids can be contacted with the body part of the user. In some embodiments, the liquid to be absorbed by the sheet for subsequent contact with the user may contain a humectant. The humectant may be selected from the group consisting of propylene glycol, sodium PCA, sodium lactate, and butylene glycol. For use in eye therapy, it is preferable that the humectant not exceed 2 weight percent of a solution to be absorbed.

In other embodiments, the solution to be absorbed by the sheet for subsequent contact with the user may include one or more of allantoin, green tea extract, ascorbate, aloe vera, chamomile extract, cucumber extract, and tea tree oil. In other embodiments, the solution to be absorbed may include a scent, such as a scent used in aromatherapy. In other embodiments, the solution to be absorbed may include pharmaceutical therapeutic agents.

The instant compress system 10 may be part of a kit that includes the frame 100, at least one gel pack 202, and at least one strap assembly 300, as well as one or various non woven sheets containing the above agents. Additionally, a compress system kit may include a case. The case may serve multiple purposes, including storing and transporting the compress system, and serving as a receptacle for heating or cooling the gel pack.

Figure 17:
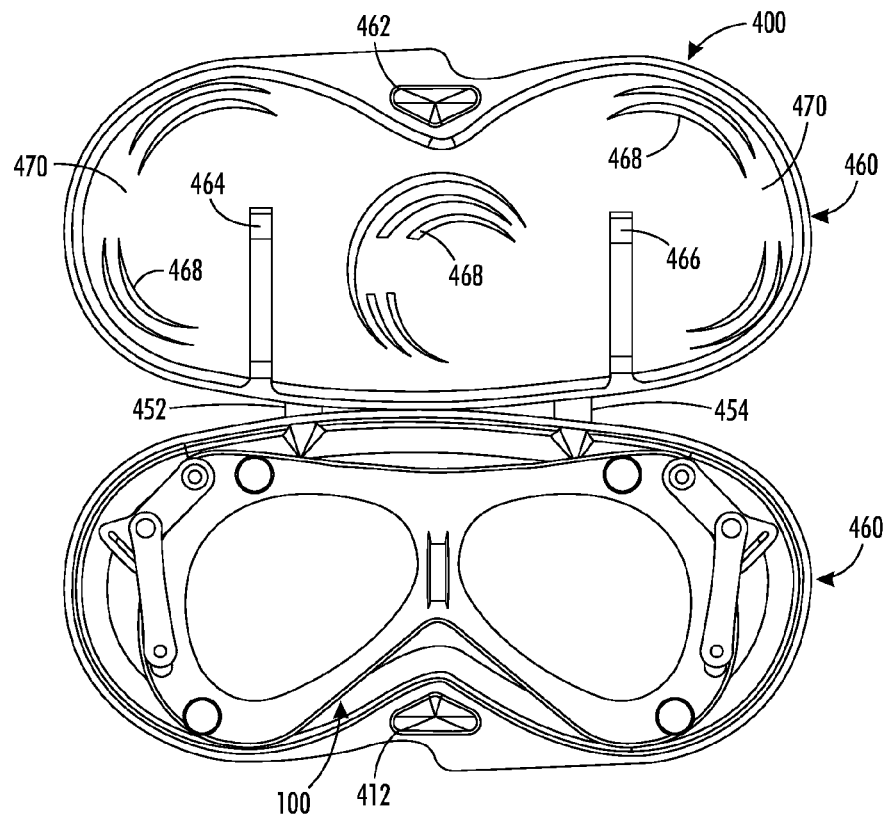
FIG. 17 is a plan view of the storage case as shown in FIG. 16, but with a frame assembly disposed in a storage compartment of the case.
Figure 18:
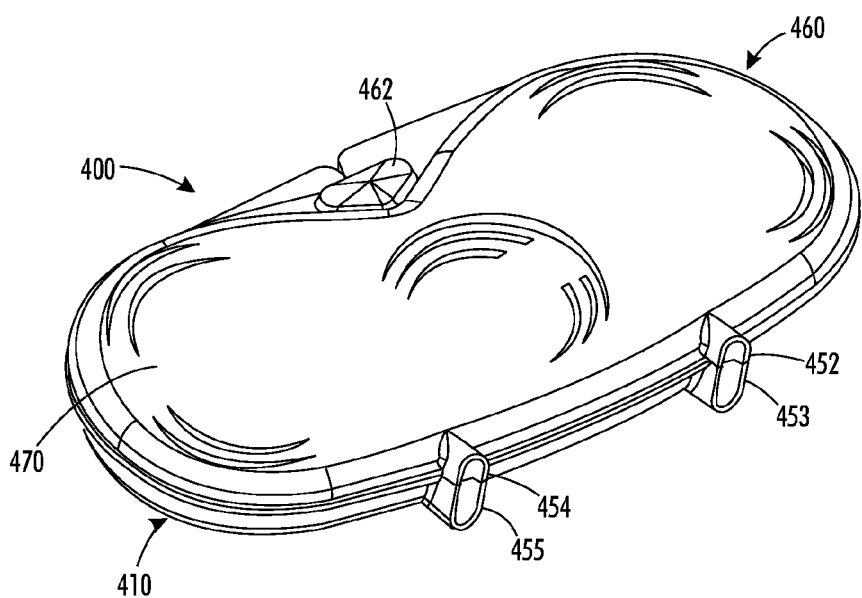
FIG. 18 is a rear perspective view of the storage case of FIG. 15 shown in the closed position.

One exemplary storage case and its uses are depicted in FIGS. 15-18. Case 400 is comprised of a bottom portion 410 hingably joined to a top portion 460. The hinges 452 and 454 of the case 400 may be made flat on their exterior edges so as to provide a pair of flat surfaces 453 and 455 when the case is closed as shown in FIG. 18. In that manner, in the closed position, the case can be set on edge upright for storage in a compact space. The case 400 may further include an integrally formed snap protrusion 412 which mates with a corresponding snap socket 462 to secure the case in a closed state.

The frame 100 of the compress system 10 may be stored in the bottom 410 of the case 400, as shown in FIG. 17. The bottom 410 may be provided with sufficient volume so as to provide room to store a gel pack 202 (not shown, see FIGS. 1, 2, and 5A), and a strap assembly (not shown, see FIGS. 6A-8). The bottom may also be used as a receptacle immediately prior to the use of the compress system 10 by a user. The user may place the gel pack 202 into the bottom, and then pour a hot or cold liquid into the bottom. The liquid then transfers heat to or receives heat from the gel pack 202, thereby heating or cooling the gel pack, which can then be snapped to the frame 100, and the system 10 donned by the user. The side wall 414 of the bottom 410 may be provided with a "fill line" marker or indicia 416, so that a user knows how much liquid to add to the bottom to submerge a gel pack.

The top 460 of the case 400 may be provided with one or more tines or clips 464 and 466, which can be used to retain at least one fabric sheet (not shown) for subsequent use with the gel pack 202 as previously described. The top 460 of the case 400 may be provided with one or more vent apertures 468 through the wall 470 of the case, which may be configured in an ornamental pattern.

It is, therefore, apparent that there has been provided, in accordance with the present invention, a therapeutic compress system and methods of using such to provide therapeutic benefit to a portion of a user's body. Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims.

I claim:

1. A support assembly for a therapeutic compress system, the assembly comprising:
 a) a deformable frame disposable upon an eye region of a human user and comprising an inner side and an outer side, a first frame section joined to a second frame section at a central bridge, and means for attachment to a gel pack disposable on the inner side of the frame;
 b) a strap assembly comprising:
  i) a first V-subassembly comprised of a first inelastic upper member joined at an inner end thereof to an upper lateral portion of the first frame section, and including an outer end, and a first elastic lower member joined at an inner end thereof to a first lower lateral portion of the first frame section and joined at an outer end thereof to a first location on the first inelastic upper member anterior to the outer end of the first inelastic member, the first inelastic upper member and the first elastic lower member forming a first apex located at the junction of the first location and the outer end of the first elastic lower member; and
  ii) a second V-subassembly comprised of a second inelastic upper member joined at an inner end thereof to an upper lateral portion of the second frame section, and including an outer end, and a second elastic lower member joined at an inner end thereof to a second lower lateral portion of the second frame section and joined at an outer end thereof to a second location on the second inelastic upper member anterior to the outer end of the second inelastic member;
 wherein during use of the assembly by the user, the first and the second upper lateral frame sections are superior to the level of the eyes of the user, and the first and the second lower lateral frame sections are inferior to the lever of the eyes of the user when the therapeutic compress system is positioned against an eye region of the user.

2. The support assembly of claim 1, further comprising an elastic connecting strap subassembly comprising a first elastic connecting strap having an inner end and an outer end, the inner end of the first elastic connecting strap joined to the outer end of the first inelastic member, and a second elastic connecting strap having an inner end and an outer end, the inner end of the second elastic connecting strap joined to the outer end of the second inelastic member, wherein the outer ends of the first and second elastic connecting straps are configured to couple to one another behind the head of the user of the assembly.

3. The support assembly of claim 2, wherein the first frame section is further comprised of a central lateral portion located between the upper lateral portion of the first frame section and the lower lateral portion of the first frame section; and wherein the second frame section is further comprised of a central lateral portion located between the upper lateral portion of the second frame section and the lower lateral portion of the second frame section; and wherein the central lateral portions of the first frame section and the second frame section are configured to deform convexly away from the eye region of the user when the deformable frame is secured against the eye region of the user and tension is applied rearwardly relative to an eye region of the user by the connecting strap, when the assembly is secured against the eye region of the user.

4. The support assembly of claim 1, wherein the first frame section includes a first internal periphery defining a first aperture, and the second frame section includes a second internal periphery defining a second aperture, and wherein when the support assembly is disposed against the eye region of the user, the first internal periphery circumscribes a portion of a first eye of a user from an anterior perspective and the second internal periphery circumscribes a portion of a second eye of the user from an anterior perspective.

5. The support assembly of claim 1, further comprising a gel pack comprised of a casing forming a chamber containing gel and comprising a first section in fluid communication with a second section; wherein the first section of the gel pack is configured to be positioned anterior to a first eye of a user, and the second section of the gel pack is configured to be positioned anterior to a second eye of the user, such that gel-containing portions of the gel pack are positioned substantially anterior to both the first eye and the second eye of the user when the assembly disposed upon the eye region of the user.

6. The support assembly of claim 5, wherein the deformable frame has exactly four male-female snap fasteners configured to couple to four male-female snap attachments on the gel pack.

7. The support assembly of claim 5, further comprising at least one moist disposable non-woven fibrous fabric sheet configured to be removably positioned between the eye region of the user and the gel pack, wherein the sheet is removable from the surface of the gel pack.

8. The support assembly of claim 7, further comprising a plurality of sheets contained within a dispenser.

9. The support assembly of claim 7, wherein the sheet is substantially rectangular and is configured to overlie first and second eyes of a user, such that the sheet is positioned substantially anterior to the first and second eyes of the user when the assembly is secured against the eye region of the user.

10. The support assembly of claim 7, wherein the sheet is configured to be sandwiched between the gel pack and the eye region of the user, when the support assembly is secured against the eye region of the user.

11. The support assembly of claim 1, wherein during use of the assembly by the user, the first apex is positioned substantially anterior to a helix of a first ear of the user, and the second apex is positioned substantially anterior to a helix of a second ear of the user.

12. A support assembly for a therapeutic compress system, the assembly comprising:
   a) a deformable frame disposable upon an eye region of a human user and comprising an inner side and an outer side, a first frame section joined to a second frame section at a central bridge, and means for supporting a gel pack, the frame having a surface area;
   b) a gel pack joined to the inner side of the deformable frame and comprised of a casing forming a chamber containing gel and comprising a first section in fluid communication with a second section, wherein the first section is configured to be positioned anterior to a first eye of the user, and the second section is configured to be positioned anterior to a second eye of the user during use of the assembly by the user; and wherein the gel pack has a surface area, and wherein the gel pack surface area is greater than the frame surface area; and
   c) a strap assembly comprising:
      i) a first V-subassembly comprised of a first inelastic upper member joined at an inner end thereof to an upper lateral portion of the first frame section, and including an outer end, and a first elastic lower member joined at an inner end thereof to a first lower lateral portion of the first frame section and joined at an outer end thereof to a first location on the first inelastic upper member anterior to the outer end of the first inelastic member, the first inelastic upper member and the first elastic lower member forming a first apex located at the junction of the first location and the outer end of the first elastic lower member; and
      ii) a second V-subassembly comprised of a second inelastic upper member joined at an inner end thereof to an upper lateral portion of the second frame section, and including an outer end, and a second elastic lower member joined at an inner end thereof to a second lower lateral portion of the second frame section and joined at an outer end thereof to a second point on the second inelastic upper member anterior to the outer end of the second inelastic member, the second inelastic upper member and the second elastic lower member forming a second apex located at the junction of the second location and the outer end of the second elastic lower member.

13. The support assembly of claim 12, wherein when the assembly is fitted to the head of the user with the gel pack disposed on the eye region of the user, the upper lateral portion of the first frame section and the upper lateral portion of the second frame section are positioned substantially superior to the level of the eyes of the user.

14. The support assembly of claim 12, wherein when the assembly is fitted to the head of the user with the gel pack disposed on the eye region of the user, the lower lateral portion of the first frame section and the lower lateral portion of the second frame section are positioned substantially inferior to the level of the eyes of the user.

15. The support assembly of claim 12, further comprising a connecting strap joined to the outer end of the first inelastic member and the outer end of the second inelastic member and configured to be positioned substantially posterior to the head of the user when the assembly is fitted to the head of the user with the gel pack disposed on the eye region of the user.

16. The support assembly of claim 15, wherein the first frame section is further comprised of a central lateral portion located between the upper lateral portion of the first frame section and the lower lateral portion of the first frame section; and wherein the second frame section is further comprised of a central lateral portion located between the upper lateral portion of the second frame section and the lower lateral portion of the second frame section; and wherein the central lateral portions of the first frame section and the second frame section are configured to deform convexly away from the eye region of the user when the deformable frame is secured against the eye region of the user and tension is applied rearwardly relative to an eye region of the user by the connecting strap, when the assembly is secured against the eye region of the user.

17. The support assembly of claim 12, wherein the means for support for the gel pack comprises four male-female snap fasteners disposed on the rear surface of the frame, and wherein the gel pack comprises four mating male-female snap fasteners disposed on a surface of the gel pack.

18. The support assembly of claim 12, further comprising at least one moist disposable non-woven fibrous fabric sheet configured to be removably positioned between the eye region of the user and the gel pack, wherein the sheet is removable from a surface of the casing of the gel pack.

19. The support assembly of claim 18, further comprising a plurality of sheets contained within a dispenser.

20. The support assembly of claim 18, wherein the sheet is in a substantially rectangular configuration and is configured to cover first and second eyes of a user, and wherein the sheet is configured to be sandwiched between the gel pack and the eye region of the user, when the support assembly is secured against the eye region of the user.

21. The support assembly of claim 12, wherein during use of the assembly by the user, the first apex is positioned substantially anterior to a helix of a first ear of the user, and the second apex is positioned substantially anterior to a helix of a second ear of the user.

22. A support assembly for a therapeutic compress system, the assembly comprising:
   a) a deformable frame disposable upon an eye region of a human user and comprising an inner side including means for attachment to a gel pack and an outer side, a first frame section including a first internal periphery defining a first aperture, the first frame section joined at a central bridge to a second frame section including a second internal periphery defining a second aperture, wherein when the support assembly is disposed against the eye region of the user, the first internal periphery circumscribes an area substantially anterior to a first eye of a user, the second internal periphery circumscribes an area substantially anterior to a second eye of a user, the first and the second upper lateral frame sections are superior to the level of the eyes of the user, and the first and the second lower lateral frame sections are inferior to the level of the eyes of the user;

b) a strap assembly comprising:
  i) a first V-subassembly comprised of a first inelastic upper member joined at an inner end thereof to an upper lateral portion of the first frame section, and including an outer end, and a first elastic lower member joined at an inner end thereof to a lower lateral portion of the first frame section and joined at an outer end thereof to the outer end of the first inelastic member, the first V-subassembly having a first apex defined by an angle formed by the first inelastic upper member and the first elastic lower member;
  ii) a second V-subassembly comprised of a second inelastic upper member joined at an inner end thereof to an upper lateral portion of the second frame section, and including an outer end, and a second elastic lower member joined at an inner end thereof to a lower lateral portion of the second frame section and joined at an outer end thereof to the outer end of the second inelastic member; the second V-subassembly having a second apex defined by an angle formed by the second inelastic upper member and the second elastic lower member; and c) a connecting strap joined to the outer end of the first inelastic member and the outer end of the second inelastic member;

wherein the first frame section is further comprised of a central lateral portion located between the upper lateral portion of the first frame section and the lower lateral portion of the first frame section, and the second frame section is further comprised of a central lateral portion located between the upper lateral portion of the second frame section and the lower lateral portion of the second frame section; and wherein the central lateral portions of the first frame section and the second frame section are configured to deform convexly away from the eye region of the user when the deformable frame is secured against the eye region of the user and tension is applied rearwardly relative to the eye region of the user by the connecting strap when the assembly is secured against the eye region of the user.

23. The support assembly of claim 22, further comprising a gel pack comprised of a casing forming a chamber containing gel and further comprising a first section in fluid communication with a second section; wherein the first section of the gel pack is configured to be positioned anterior to a first eye of a user, and the second section of the gel pack is configured to be positioned anterior to a second eye of the user, such that gel-containing portions of the gel pack are positioned substantially anterior to both the first and second eyes of the user when the assembly is disposed upon the eye region of the user.

24. The support assembly of claim 22, further comprising at least one moist disposable non-woven fibrous fabric sheet configured to be removably positionable between the eye region of the user and the gel pack, and wherein the sheet is substantially rectangular and is configured to cover first and second eyes of a user, and be sandwiched between the gel pack and the eye region of a user, when the support assembly is secured against the eye region of the user.

25. The support assembly of claim 22, wherein during use of the assembly by the user, the first apex is positioned substantially anterior to a helix of a first ear of the user, and the second apex is positioned substantially anterior to a helix of a second ear of the user.

* * * * *